United States Patent [19]

Thurston et al.

[11] Patent Number: 5,441,050
[45] Date of Patent: Aug. 15, 1995

[54] RADIATION RESPONSIVE SURGICAL INSTRUMENT

[75] Inventors: Marlin O. Thurston, Columbus; Karl W. Olson, Worthington, both of Ohio

[73] Assignee: Neoprobe Corporation, Dublin, Ohio

[21] Appl. No.: 992,622

[22] Filed: Dec. 18, 1992

[51] Int. Cl.⁶ .............................................. A61B 6/00
[52] U.S. Cl. .................................. 128/659; 128/654; 250/370.01; 250/370.13; 250/370.15
[58] Field of Search ....................... 128/653.1, 654, 659; 250/370.01, 370.07, 370.13, 370.15

[56] References Cited

U.S. PATENT DOCUMENTS

| | | | |
|---|---|---|---|
| 4,695,730 | 9/1987 | Noda et al. | 250/370 |
| 4,782,840 | 11/1988 | Martin, Jr. et al. | 128/654 |
| 4,801,803 | 1/1989 | Denen et al. | 250/336 |
| 4,889,991 | 12/1989 | Ramsey et al. | 250/336.1 |
| 4,932,412 | 6/1990 | Goldenberg | 128/654 |
| 5,070,878 | 12/1991 | Denen | 128/659 |
| 5,151,598 | 9/1992 | Denen | 250/336.1 |
| 5,152,293 | 10/1992 | Vonesh et al. | 128/662.03 |

OTHER PUBLICATIONS

"CdZnTe Gamma Ray Detector" by Butler et al.
Recent Developments in CdZnTe Gamma Ray Detector Technology by Butler, et al.
Properties of CdZnTe Crystals Grown by a High Pressure Bridgman Method by Doty et al.
Semi–Conductor Nuclear Particle Detectors and Circuits, pp. 476–483 Proceedings–Sub. Committee on Instruments and Techniques Committee on Nuclear Science (1969).

Primary Examiner—Ruth S. Smith
Attorney, Agent, or Firm—Mueller and Smith

[57] ABSTRACT

A crystal containing detector particularly suited for use in immunoguided surgery capable of detecting gamma emissions present at tumor sites. The instrument utilizes a cadmium-zinc-telluride detector crystal which may be retained within a finger mount positioned over the surgeon's finger. Within this mount there also is incorporated a first preamplification stage designed to accumulate charge signals from the detector as well as to drive a relatively short length of cable to a second preamplification stage located, for example, within a housing at the surgeon's upper arm. The small finger mounted probe may be moved between operative orientations at the underside of the tip of the finger to stand-by orientations at the top of the finger adjacent the knuckles. In an additional embodiment, the finger probe incorporates a sodium iodide crystal, the scintillations from which are transmitted via a short length of fiber optic cable to an upper arm mounted housing which contains a photomultiplier tube. Signals from the remote, arm-mounted housing then are transmitted via longer cabling or the like to a control console.

22 Claims, 10 Drawing Sheets

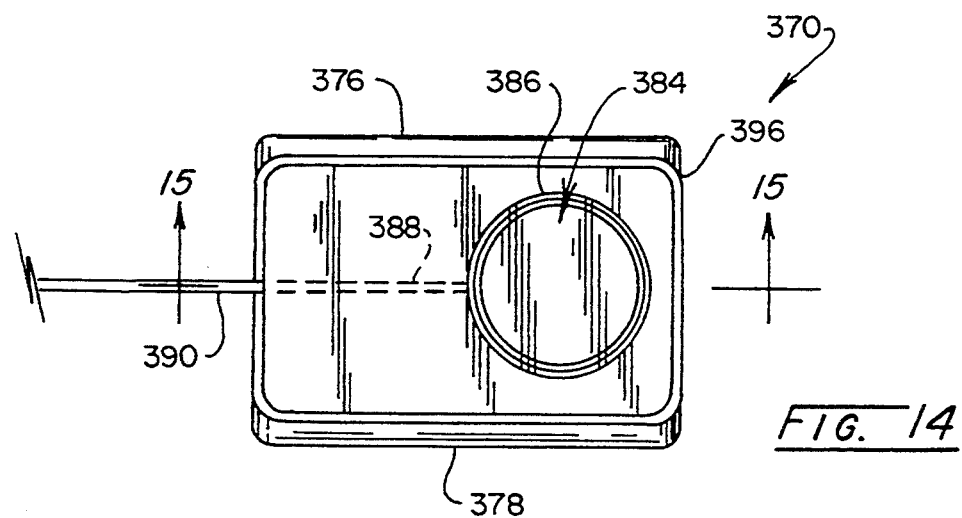
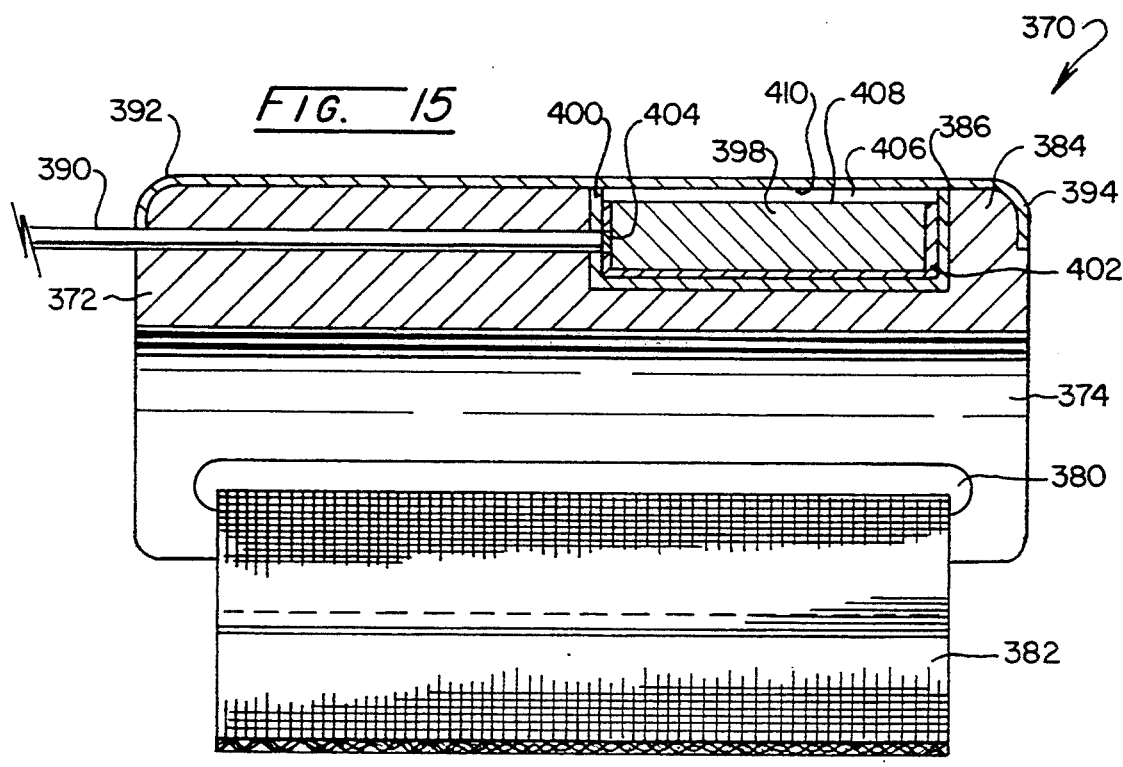

RADIATION RESPONSIVE SURGICAL INSTRUMENT

BACKGROUND OF THE INVENTION

Current and historical procedures for the treatment of colon and rectal cancer have been based upon the natural history of tumor spread, and thence, upon operative and non-operative options. Operative options generally have looked to the physical location and surgical resection of tumor. A variety of techniques have been brought to bear in the art with the purpose of aiding the surgeon in detecting and localizing neoplastic tissue as part of this surgical procedure. ("Neoplastic tissue", for present purposes, often is referred to as cancerous tissue, though malignant tumor and malignant tumor cells also are found in the terminology of the art. The term "neoplastic tissue" includes all of these.) A substantial amount of effort in aiding the surgeon in locating neoplastic tissue has been through the utilization of radiolabeled antibody for detection purposes. For example, one technique includes the scintillation scanning of patients injected with relatively high energy, e.g. $^{131}I$ labeled antibodies. Such photoscanning or scintillation scanning provides scintigrams difficult to interpret or of little value for detection of small lesions because of blood pool background radioactivity. Computer subtraction of radioactive blood pool agents and the use of two labeled antibodies (one specific for the tumor and one non-specific) have been attempted to enhance imaging. Nevertheless, such techniques have been found to provide little, if any, useful information to the surgeon, especially over and above CAT scans, magnetic resonance imagings, and like traditional techniques. Typically, large tumor is readily located by the surgeon by visualization at the operating theater as well as through palpation, i.e. the feel of a tumor as opposed to that of normal tissue. To achieve operative success, however, it is necessary for the surgeon to somehow locate neoplastic tissue at positions within the body cavity not accessible with vision, for example internally within the pelvic region or behind the liver or pancreas. It also is necessary for the surgeon to locate "occult" tumor at any position. Occult tumor or occult neoplastic tissue is that which is so diminutive in size as to be unidentifiable either by sight or feel. Failure to locate and remove such occult and non-visible tumors generally will result in the continued growth of cancer in the patient, a condition often misidentified as "recurrent" cancer. In general, conventional diagnostic techniques as, for example, use of the classic gamma camera and the like, fail to find or locate occult tumor. As tumor sites become smaller, the radionucleide concentrations at a given tumor site will tend to be lost, from an imaging standpoint, in the background radiation necessarily present.

U.S. Pat. No. 4,782,840 by Martin, M.D. and Thurston, Ph.D., entitled "Method for Locating, Differentiating, and Removing Neoplasms", issued Nov. 8, 1988 (the disclosure of which is expressly incorporated herein by reference) reviews such scintillation scanning technique and discloses a much improved method for locating, differentiating, and removing neoplasms. Such technique utilizes a radiolabeled antibody and a portable radiation detection probe which the surgeon may use intraoperatively in order to detect sites of radioactivity. Because of the proximity of the detection probe to the labeled antibody, the faint radiation emanating from neoplastic tissue at occult sites becomes detectable, for example, in part because of the inherent application of the approximate inverse square law of radiation propagation. The procedure is known as the Radioimmunoguided Surgery TM system (Radioimmunoguided Surgery being a trademark of Neoprobe Corporation, Columbus, Ohio) and is successful additionally because of a recognition that tumor detection should be delayed until the blood pool background of circulating radiolabeled antibody has had an opportunity to be cleared from the body. As a consequence, the photon emissions or radiation emitted by minor tumors compared to surrounding tissue becomes detectable in view of the proximity of the probe device to it. Fortuitously, the '840 patent discloses the ability of the radiolabeled antibody to remain bound to or associated with neoplastic tissue for extended periods of time with the radio tag still bound thereto. Moreover, even though the accretion of radioactivity at the tumor site decreases over time, the blood pool background and surrounding tissue (relative to the tumor sites) decrease at a much greater rate so that the radioactive sites can be determined readily utilizing a hand held probe positioned in close proximity with the tissue under investigation. Also discussed in the '840 patent is the improved inventive methodology focused upon lower level energy isotopes exhibiting photon emissions of energy levels less than about 300 Kev advantageously and, preferably, less than about 150 Kev.

The instrumentation developed to support the radioimmunoguided surgery system has been called upon to meet rigorous performance criteria. Radiation emitted from occult tumor necessarily is very sparse and will emit to evoke a relatively low count rate upon detection. This low count rate, in turn, is developed with a corresponding count rate from the same radioisotope which is background radiation, albeit in itself low, but which must be accommodated for. The circuitry involved for such instrumentation is described, for example, in U.S. Pat. No. 4,801,803 by Denen, et al., entitled "Detector and Localizer for Low Energy Radiation Emissions", issued Jan. 31, 1989. To evaluate detected emissions and the counts generated therefrom with the instrumentation, a microprocessor-driven control program has been developed as is described in U.S. Pat. No. 4,889,991, by Ramsey, et al., entitled "Gamma Radiation Detector with Enhanced Signal Treatment", issued Dec. 26, 1989.

This instrumentation supporting the probe device which is held by the surgeon and maneuvered within the body cavity is retained within a battery-powered console located within the operating room. Because of the low levels of signal evoked at the crystal detector within the probe, that device itself carries a preamplification stage for the purpose of generating a signal output suitable for transmission by cable or the like to the adjacent console. The preamplification stage performs in conjunction with a cadmium telluride crystal detector, and this combination of components is called upon to perform at the temperatures of the human body while undergoing calibration at substantially cooler temperatures found, for example, in the operating room environment. This requirement has tended to reduce the energy level discrimination flexibility of the devices. The architecture of the hand-held probe, particularly as it is concerned with the noise-free mounting of the cadmium telluride crystal, has been described, for example, in the noted U.S. Pat. Nos. 4,801,803, 4,893,013, by Denen, entitled "Detector and Localizer for Low Energy Radiation Emissions", issued Jan. 9, 1990, and in U.S. Pat. No. 5,070,878, by Denen, entitled "Detector and Localizer for Low Energy Radiation Emissions", issued Dec. 10, 1991. The probe so described has an overall length of about 15 cm; is tubular in cross section, and has a forward tip portion canted at an angle of about 30° to aid the surgeon in maneuvering it within the body cavity. Where such maneuvering requires access to tissue adjacent the pelvis or behind the liver or pancreas, even this relatively small hand-held probe may become difficult for the surgeon to position as desired. Once the surgeon has located neoplastic tissue at these hidden locales, it may be desirable then to use the remaining available perception of feel for the purpose of additional verification of a tumor site. However, where the hand is called upon to grasp the tubular handle component of the probe, this surgical exercise may become difficult.

SUMMARY

The present invention is addressed to apparatus and instrumentation for locating sources of radiation emissions which exhibit improved detecting capability both from the aspect of crystal response and with respect to the accessing of radiation sources. Crystal response and corresponding instrument performance is enhanced through the utilization of a cadmium-zinc-telluride crystal detector. This improved detector performance is complemented with an improved preamplifier. The cadmium-zinc-telluride crystal detector exhibits an output stability improved over the temperature excursions typically encountered within an operating room environment. In complement, the improved preamplifier achieves gain stability under temperature variations as well as an operation exhibiting low noise characteristics. Because of the improved operational aspects of the cadmium-zinc-telluride crystal for the instrumentation at hand, the mounting architecture thereof may be somewhat simplified as compared to previous instrumentation utilizing non-alloyed cadmium telluride crystals. This, in turn, permits the implementation of the crystals within probe devices having quite variant structuring, including diminutive sizes.

To achieve improved surgical access to remote body regions, the probe or instrument of the invention is configured with a finger mount which is slidably retained on a select finger of the surgeon, for example the second finger. In this regard, the device may be moved forwardly upon that finger to an operative position where the detection components are at the underside of the finger. When so held, stability is imparted to the device by the abutment of adjacent fingers upon guideways formed along the sides of the probe. The probe configuration also permits easy maneuvering of the instrument to a stand-by orientation at the upper side of the mounting finger at a rearward location adjacent the surgeon's knuckles. This stand-by orientation permits flexure of the hand for palpation procedures and the like while holding the probe at a convenient location where it readily is transferred back to an operational orientation.

To achieve the requisite diminutive size required for finger mounting using practical electronic design, a split preamplification feature is presented. With this arrangement, the finger mount carries a first preamplification stage including a charge accumulation network and an amplification stage which, in turn, is configured for conveying crystal derived signals over a relatively short length of cable. That cable of restricted length extends, for example, to a circuit housing attached to the surgeon's arm in the vicinity of the shoulder. Within that remote housing, additional amplification stages are installed for effecting signal transmission over somewhat lengthy shielded cable to a control console. These latter, relatively higher gain amplification stages exhibit temperature compensation attributes to stabilize gain performance. Of further advantage, these remotely located amplification stages are within a somewhat stable temperature environment away from heat exchange with the warmer surgeon's hand and patient's body.

In an alternate embodiment of the finger mounted probe, a sodium iodide crystal is employed in conjunction with a relatively short length of fiber optic transmission cable. This cable extends, as before, to a small housing mountable upon the surgeon's arm in the vicinity of the shoulder. However, the housing now contains a small photo-multiplier tube for conversion of scintillation-based data signals as received from the fiber optic bundle to electrical transmit signals. Isolation of the photo-multiplier tube is initially desirable for this embodiment inasmuch as such devices require relativley higher voltages which would not be desirable within instrumentation positioned closely adjacent a patient or within that patient's body cavity.

Other objects of the invention will, in part, be obvious and will, in part, appear hereinafter.

The invention, accordingly, comprises the apparatus and technique possessing the construction, combination of elements and arrangement of parts which are exemplified in the following detailed disclosure. For a fuller understanding of the nature and objects of the invention, reference should be had to the following detailed description taken in connection with the accompanying drawings.

BRIEF DESCRIPTION OF THE DRAWINGS

FIG. 14 is a top view of another embodiment of a finger mounted probe according to the invention with a cap portion removed to reveal internal structure; and FIG. 15 is a sectional view taken through the plane 15—15 shown in FIG. 14.

DETAILED DESCRIPTION

Figure 1:
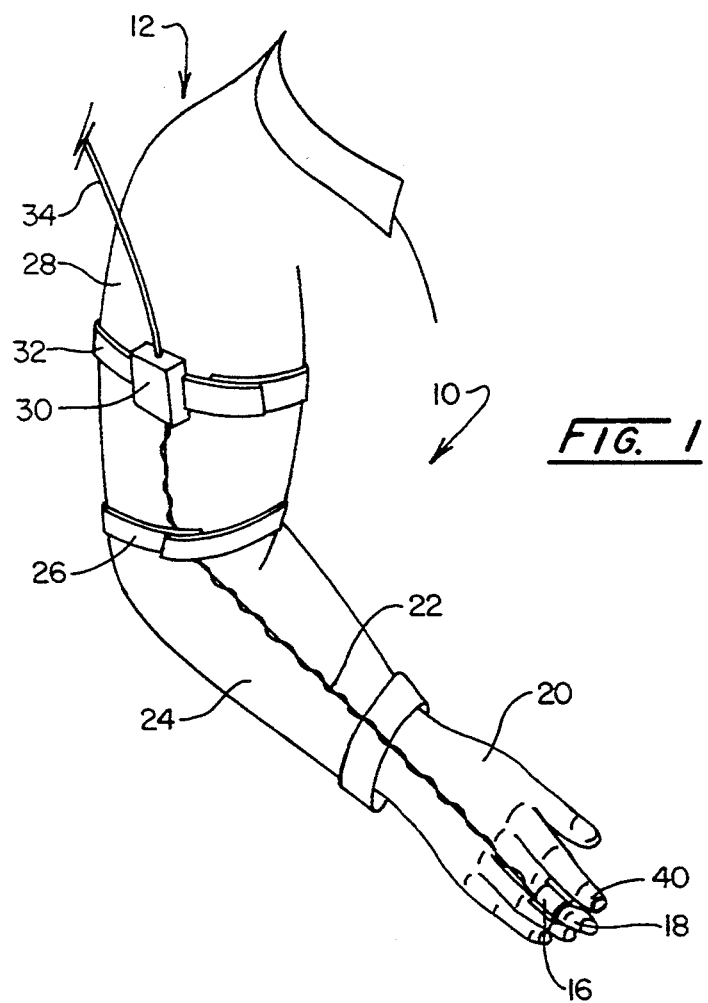
FIG. 1 is a perspective view of a surgeon's hand, arm, and shoulder showing the mounting of a probe according to the invention.

The general RIGS procedure commences with the administration to the patient of an effective amount of a radiolabelled locator which specifically binds a marker produced or associated with neoplastic tissue. A "locator" includes a substance which preferentially concentrates at tumor sites by binding with a marker (the cancer cell or product of the cancer, for example) produced by or associated with neoplastic tissue or neoplasms. Appropriate locators today primarily include antibodies (whole and monoclonal), antibody fragments, chimeric versions of whole antibodies and antibody fragments, and humanized versions thereof. It should be appreciated, however, that single chain antibodies (SCAs such as disclosed in U.S. Pat. No. 4,946,778) and like substances have been developed and they primarily prove efficacious. Biochemistry and genetic engineering may yet produce substances which mimic the function of antibodies in selectively concentrating at sites of neoplastic tissue, though such substances may not be subsumed within the traditional definition of "antibody". "Locator" is a term chosen to include present-day antibodies and equivalents thereof, as well as those substances yet to be determined which mimic antibodies in the method of the RIGS system.

The carrying out of radioimmuno-guided surgical techniques (RIGS) calls for a certain dexterity on the part of the surgeon in maneuvering the crystal containing probe in close proximity and at proper rates along the tissue under investigation. The probe, which is hand-held by the surgeon, will have a window surface behind which is located a detector such as a cadmium telluride crystal. Because the RIGS surgical approach is one wherein the extent of radiation emanating from the locator positioned at neoplastic tissue is quite faint, it becomes necessary that a close proximal association be established between that probe and such tissue. Because of the rapid fall-off of radiation as the crystal surface is moved away from such a tissue region in consequence of the inverse square law of radiation propagation, it is essential that the surgeon maintain this close proximity between the crystal surface and tissue at which radioactive locator is concentrated. The probe window, of course, protects the crystal surface from the tissue and its environment. In effect, this application of the inverse square law of radiation propagation aids in sharply delineating the extent or boundaries of neoplastic tissue. Collimators obviously are not employed with such a system where low energy radiation is involved, inasmuch as they would not sharpen the location of radiation but would lessen the number of received emissions from the hint radiation source at the tumor site. It is apparent, therefore, that a facility of maneuverability of these probes becomes an important aspect of the surgical procedure. Using conventional probe structures, such maneuverability becomes difficult as the surgeon must probe the pelvic region or regions behind the pancreas or liver. As this region is accessed, the surgeon loses the perceptive aspect of sight and must then rely upon the perception of feel and enhancement of that perception with the RIGS system. For very small tumor size, i.e. occult tumor, the sense of touch or feel is reduced or lost within inaccessible areas and the value of the RIGS system becomes apparent. However, indications of occult tumor within such difficult to access regions should permit the surgeon's hand to manipulate the tissue found suspect following the indication of tumor by the hand retained probe. This requisite flexibility and accessibility is achieved with the present invention by a probe design which is configured to be carried and supported by a finger of the surgeon and which in the course of difficult accessing procedure may be moved between active detecting and stand-by positions, the latter positions permitting essentially full hand maneuverability at the site of tissue investigation.

Referring to FIG. 1, a probe assembly according to the invention is represented generally at 10 as it is carried by a surgeon represented schematically at 12. The probe or probe component of the assembly 10 is shown at 16 being slidably mounted on the second finger 18 of the hand 20 of surgeon 12. Probe component 16 is represented as being in an active detection position such that it is mounted over the portion of finger 18 corresponding with one phalanx bone (connected to the tip phalanx) although location beneath a glove has been contemplated. It may, of course, be used on a different finger at the surgeon's discretion. In general, the probe 16 will be positioned over the sugical glove of the surgeon 12. Additionally outwardly of the glove is an initial length of communicating cable or wiring 22 which extends a limited distance along the forearm 24 of surgeon 12, whereupon it is secured by a strap 26 in the vicinity of the elbow joint. It then is seen to extend to the shoulder region 28 of surgeon 12 at which position a circuit housing 30 is fastened to the surgeon's arm, for example, by a strap or connector 32. From the circuit housing 30, a cable 34 extends to a battery powered console located in adjacency to the surgeon within the operating room. The transmission arrangement thus shown includes a preamplification stage (not shown) which is mounted within the probe 16 itself and which is designed to provide an amplification of its detector output suited particularly for transmission along the length of cable 22 to a second preamplification circuit retained within circuit housing 30. The latter, second preamplification stage derives a transmit output of appropriate characteristic for transmission over the relatively lengthier cable 34. This arrangement enhances the capability for structuring the necessary small or diminutive probe component 16.

Figure 2:
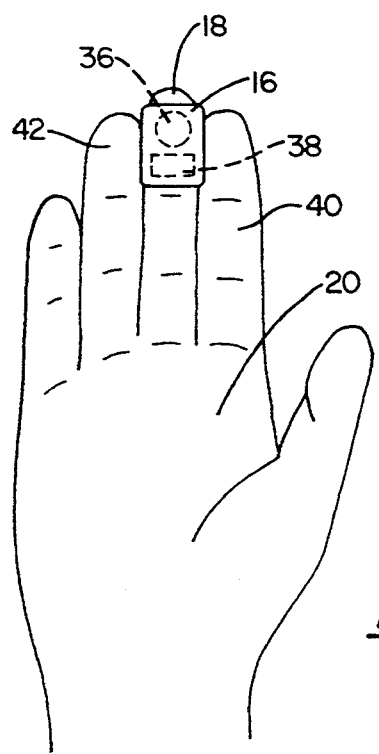
FIG. 2 is a front view of a surgeon's hand showing a probe according to the invention mounted in another operative orientation.
Figure 3:
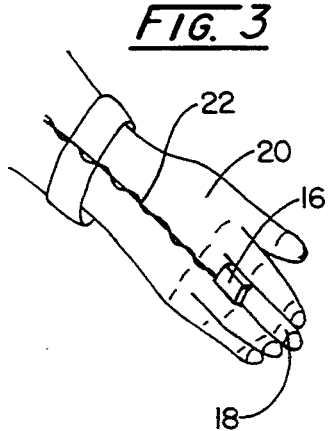
FIG. 3 is a perspective view of a hand of a surgeon showing a probe according to the invention at its stand-by orientation.

In FIG. 1, the "back" side of probe 16, which is an elastomeric strap, is seen. Looking to FIG. 2, the opposite side of this probe component 16 is revealed. Shown in FIG. 2 as being mounted at or near the tip of the underside of finger 18, i.e. adjacent or over the terminal phalanx bone, the length of probe 16 along finger 18 is about 2 cm. This short length permits retention of the device while allowing finger flexure. Shown in phantom in the figure is a cavity 36 which serves as a seat within which a crystal detector is mounted and an adjacent rectangular enclosure or cavity 38 within which the noted initial pre-amplification stage may be retained. With this configuration, it is evident that the surgeon 12 is capable of maneuvering the probe at regions of the human anatomy otherwise quite difficult to access. In the course of such utilization of the probe 16, its orientation in the hand 20 is stabilized by those fingers of the surgeon's hand 20 as at 40 and 42, the side surfaces of which press against the corresponding side surfaces of the device in a somewhat natural manner. To enhance this stability and ease in maneuver of the probe 16 about the finger 18, guideways of, for example, shallow curved configuration, extend along each side of the device 16 throughout its lengthwise extent. Thus, the surgeon can control the orientation of probe 16 by manipulation of adjacent fingers 40 and 42 with respect to finger 18. In effect, a "one-handed" manipulation capability is realized. This manipulation may carry out a rotation and translation of the probe 16 to a stand-by position upon finger 18. Such position may, for example, move the device 16 to a location over the upper side of the third phalanx adjacent the palm as shown in FIG. 3. In this stand-by orientation, the active side of the probe 16 as seen in FIG. 2 is rotated to the top of the hand 20, as well as moved backwardly toward the palm or knuckles for flexure and unhindered use of hand 20.

Figure 4:
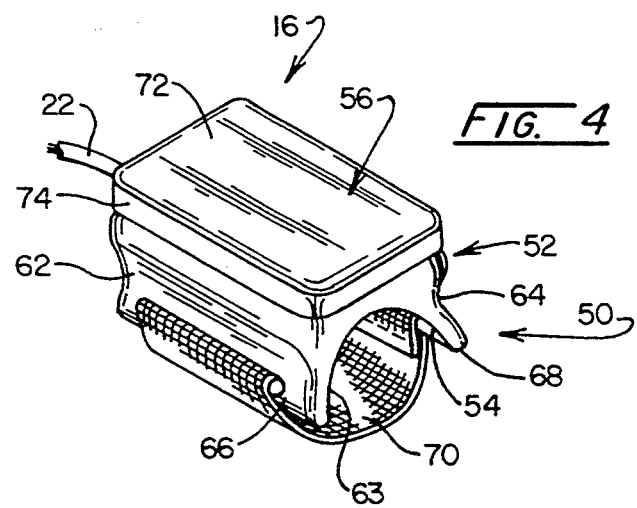
FIG. 4 is a perspective view of a probe according to the invention.

Looking to FIG. 4, the probe component 16 is shown in perspective. Probe 16 may be formed, for example, from aluminum or plastic, and is configured having a finger mount represented generally at 50 which includes a support region 52 and an oppositely-disposed concave mount portion 54. Looking additionally to FIG. 5, the support region 52 is seen to include a detector mount portion 56 and a pre-amplifier containment portion 58. Within detector mount portion 56 there is formed the earlier-noted crystal receiving cavity 36 and in adjacency thereto within the pre-amplifier containment portion 58 there is located the earlier-noted pre-amplifier containment cavity 38.

FIG. 4 reveals that the outward surface of the concave mount portion 54 is configured in concave fashion to develop the above-discussed elongate guideways 62 and 64 extending along the lengthwise extent of finger mount 50. These guideways 62 and 64 aid in maintaining and changing the orientation of the probe 16 through their abutting contact with adjacent fingers of the surgeon's hand. The internal region of the concave mount portion 54 is configured substantially as a half cylindrical surface 63 of radius selected for nesting against the surgeon's mounting finger as described at 18 in FIGS. 1–3. This surface 63 extends to two oppositely disposed strap connector portions 66 and 68. Looking additionally to FIG. 6, the strap connector portion 68 is seen to be formed as an elongate slot. Strap connector portion 66 is identically fashioned. These connector portions 66 and 68 serve to provide for the attachment of an elastomeric web-like strap 70 which functions to retain the finger mount 50 against the surgeon's hand and exhibits sufficient flexure or elasticity so as to permit the movement of the probe 16 about the finger, for example, in the orientations represented in FIGS. 1–3.

Figure 6:
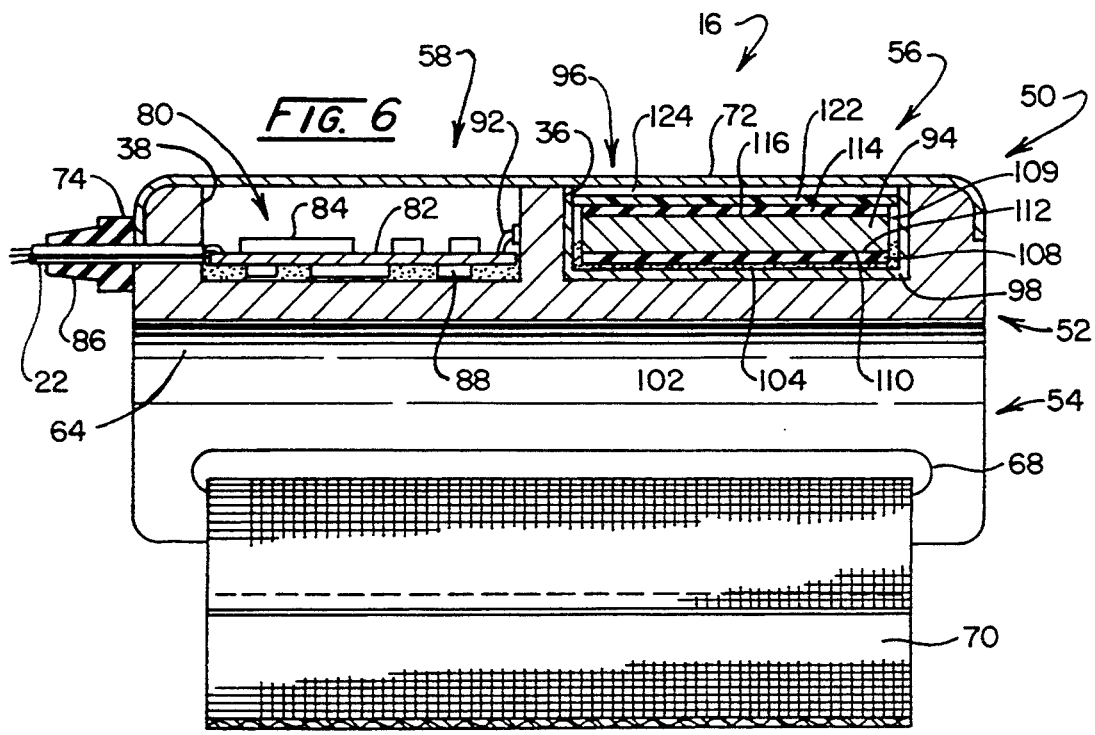
FIG. 6 is a sectional view taken through the plane 6—6 of FIG. 5.

Returning to FIG. 4, the support region 52 is seen to additionally support a cap or cover 72. This cover 72 is configured of a material and is dimensioned so as to seal the cavities 36 and 38 while permitting the ingress or passage of radiation into the detector mounted within detector cavity 36. In this regard, the cover 72 may be formed of aluminum having a thickness, for example, of about 0.01 inch (0.25 mm). FIGS. 4 and 6 show that the cover 72 is fashioned having a downwardly disposed and integrally formed flange or skirt 74 which nests over the support region 52 of finger mount 50. To seal the assembly against the incursion of contaminants such as body fluids and the like, attachment between the cover 72 and support region 52 may be provided, for example, with an epoxy cement.

Figure 5:
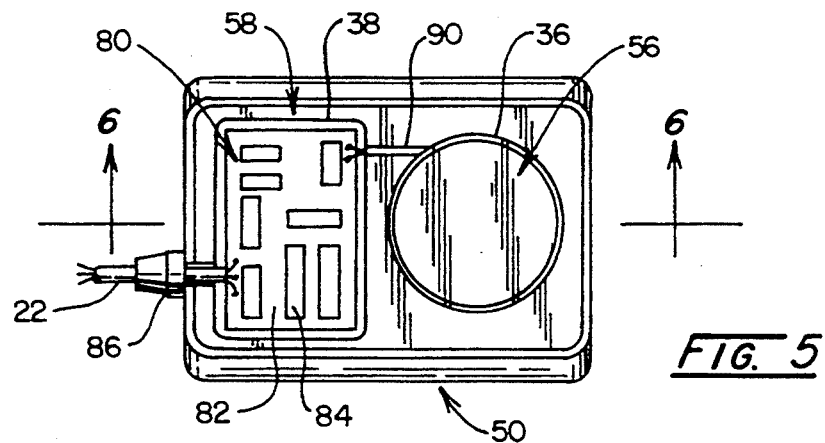
FIG. 5 is a top view of the probe of FIG. 6 with a cap component removed to reveal inner structure.
Figure 7:
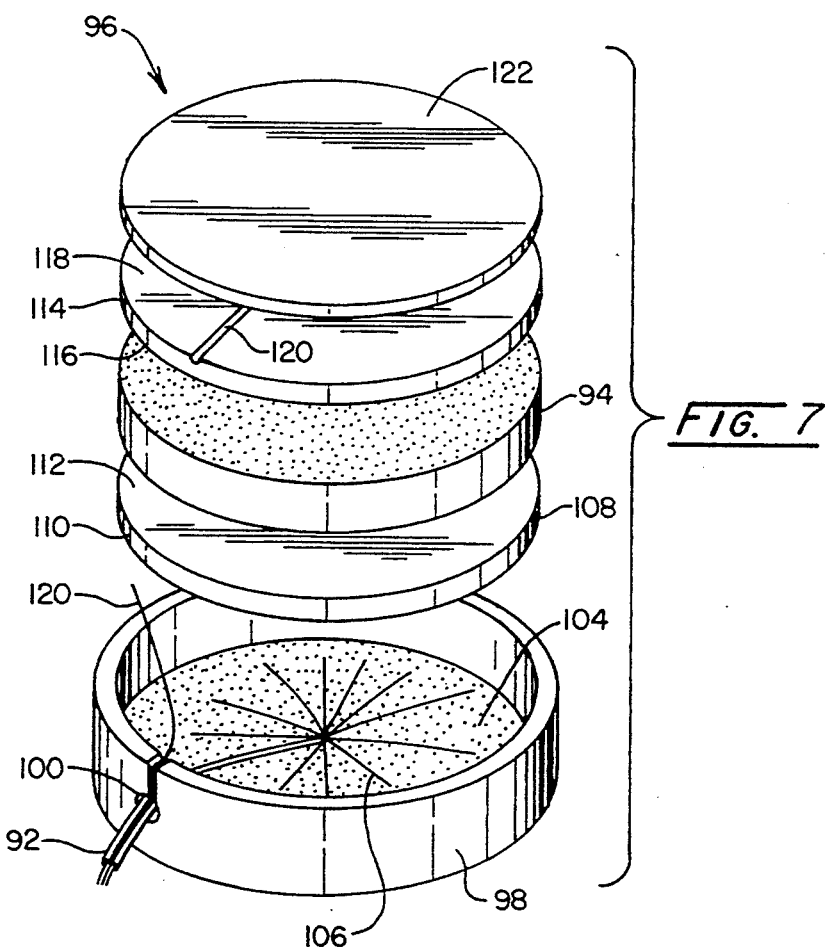
FIG. 7 is an exploded perspective view of a crystal mounting employed with the probe of FIG. 4.

FIGS. 5 and 6 reveal that the preamplifier containment portion 58 and associated cavity 38 serve to mount and retain the first preamplifier stage represented in general at 80. In order to achieve requisite small size and volume, stage 80 preferably is formed including a printed circuit board 82 which serves, in turn, to support surface mounted components, certain of which are represented at 84. Typically, the board 82 will function to mount those components on each of its oppositely disposed surfaces. Accessing the first preamplification stage 80 is the earlier-noted cable 22, the portion thereof immediately adjacent support region 52 being buttressed by a strain relief 86 formed, for example, of a soft rubber coating. Cable 22 is seen to extend through an aperture in the support region 52 for appropriate solder connections with circuit board 82. Board 82 is retained within the cavity 38 by an insulative silicon rubber compound represented at 88. Compound 88 is, for example, heat-stable silicone rubber sold under the trademark "SILASTIC". The latter product is an electrically insulative elastomeric adhesive which functions to retain its elastic properties over a broad range of environmental temperatures. The material is generally referred to as silicone rubber which is an elastomer in which the C linkages of a polymerized hydrocarbon are replaced by Si-O linkages. Electrical communication between the first preamplifier stage 80 and the detector components of probe 16 is provided through a channel or slot 90 extending between chambers 38 and 36. In this regard, a small lead assemblage is shown at 92 extending through slot 90. Looking to FIGS. 6 and 7, the assemblage providing for the retention of a CdZnTe detector crystal 94 is revealed in general at 96. The outermost component of assemblage 96 is provided as a cup-shaped crystal retainer or outer shield 98 formed of lead of relatively thin dimension, for example, having a thickness of 0.25 mm. Cup 98 may be press fitted within cavity 36 and is formed having an aperture 100 (FIG. 7) through which the lead assembly 92 may pass. Positioned over the lower surface or seat 102 (FIG. 6) of the cup 98 is a layer of the above-described silicon rubber or "SILASTIC" compound. Extending over the layer 104 are a plurality of strands 106 from a multi-strand wire within the cabling 92 functioning to provide an electrical bias for assertion against the inwardly disposed surface of crystal 94. The strands 106 of the biasing input to the assemblage are seen to be positioned over the upper surface of layer 104 such that they are electrically insulated from the seat 102 and so that they may contact a next adjacently-disposed disk shaped electrically conductive conformable cushion layer 108 having a lower disposed surface 110 positioned over the strands 106 and upon the forwardly facing surface of insulative elastomeric layer 104. The adhesive attachment between these components serves to avoid microphonically induced noise at the crystal 94. With the arrangement thus shown, electircal bias, as well as electrical communction with respect to charge transfer is asserted from the strands 106 into the electrically conductive cushion layer 108 and, thence, through freely-abutting relationship with the lower surface of crystal 94 to that component. Preferably, the electrically conductive cushion layer 108 is provided as a non-woven Teflon cloth which is carbon-filled to the extent rendering it an effective conductor of electricity. In general, the material is a carbon-containing stretched, highly crystalline, unsintered polytetrafluoroethylene marketed under the trademark "GORETEX". To avoid contamination, it is desirable that the cushion layer 108 be as pure as possible through appropriate wash-type treatment or the like. While no adhesive or the like is employed in the union between the lower surface of crystal 94 and the upwardly disposed surface of layer 108, some silicone adhesive may migrate about the edge of crystal 94 with beneficial effect, This arrangement is achieved inasmuch as the periphery of crystal 94 is spaced from the inwardly-disposed surface of cup 98 to define a gap 109 (FIG. 6).

Positioned over the upwardly-disposed surface of crystal 94 is another electrically conductive deformable layer 114. Formed, for example, of material identical to that of layer 108, layer 114 serves to cushion the upper surface of crystal 94 against vibratory induced microphonic or the like effects as well as to provide electrical contact between its lower surface 116 and the upwardly-disposed surface of crystal 94. In this regard, the electrically-conductive layer 114 functions to assert a ground by virtue of the freely-abutting contact of its upwardly disposed surface 118 with a ground lead 120 (FIG. 7) extending from the lead grouping of cable 22.

Retaining the entire assemblage including layer 104, biasing strands 106, cushioning layer 108, crystal 94, cushioning layer 114, and ground lead 120 in proper mutually abutting association as well as in a slight compression is a disk 122. Formed of radiation transmissive plastic or the like, the disk 122 is structured so as to provide a press fit within the internal surfaces of cup 98. To assure the maintenance of this compressive retention of the noted components, disk 122 may be secured adhesively utilizing the noted silicone rubber material. FIG. 6 reveals that the disk 122 retains the crystal supporting assemblage at a position below the cover 72 in a manner defining a gap 124. This gap 124 serves to isolate the crystal retaining assemblage from physical engagement with the cover 72. Gap 124 functions to provide an acoustic impedance to avoid the transmission of vibration from cover 72 which may be occasioned by the maneuvering of the probe 16 along tissue under investigation. Gap 124 is of relatively small height, for example about 0.5 mm, to assure that the forward surface of crystal 94 is as close as practical to the tissue under investigation. Such distancing of that forward surface with respect to the tissue under investigation is quite important in view of the low level of radiation involved and the noted inverse relationship of radiation propagation. In general, the user of the instrument 16 will witness a rapid fall-off of count response to radiation with the distancing of the forward surface of crystal 94 from such source.

The diminutive size of the probe 16 is achieved both with the utilization of a dual stage preamplification arrangement as well as with the more simplified crystal mounting approach thus described. This latter mounting approach is, in part, made available through the selection of a CdTe material alloyed with zinc and generally represented by the expression: $Cd_{1-x}Zn_xTe$. In general, CdTe detecting crystals exhibit benefits such as operability at room temperature, high counting rates and small size. However, for the surgical implementation at hand, they exhibit a noise evoking temperature dependence which heretofore has been accommodated for through the elevation of lower window or threshold energy levels within control circuitry. Such an approach to accommodating these attributes of the non-alloyed crystals has, in the past, called for an operational trade-off representing loss of some radiation count data. In general, cadmium telluride based instruments as employed in the operating theater are calibrated at a room or environmental temperature, for example, the temperature witnessed by the probe during calibration within an operating room may be somewhat below 15° C. (59° F.). The probe then is grasped by the surgeon, a maneuver which, in itself, will develop a higher temperature from the communication between the surgeon's hand and the probe. For the RIGS procedure, the probe is used within the body cavity where body temperature is about 39° C. Thus employed, the crystal component of the probe will more than likely reach a temperature of about 35° C. and in some instances higher. The result from this temperature excursion heretofore utilizing CdTe crystals has been a generation of crystal dominant noise for which the instrumentation has been called upon to evoke an arbitrary lower window adjustment.

Figure 8:
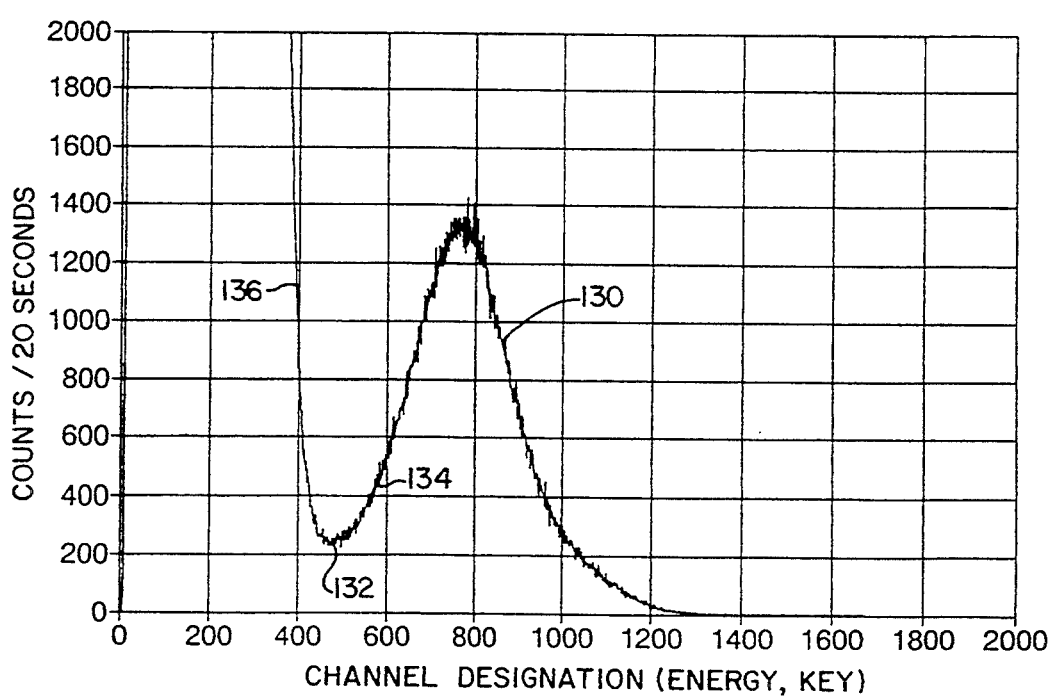
FIG. 8 is a multi-channel analyzer plot taken in conjunction with a CdTe crystal.

Looking to FIG. 8, a plot developed with a multi-channel analyzer utilizing a non-alloyed CdTe crystal in conjunction with a $^{129}I$ check source is revealed. The curve represented in the figure was developed at room temperature (20° C.) and in conjunction with a preamplifier as described in the above noted U.S. Pat. No. 4,801,803 performing in conjunction with a console also as described therein. Count values as identified along the vertical scale of the figure were developed in conjunction with the relatively lengthy count interval of 20 seconds. The horizontal scale of the figure is representative of energy and is graduated in arbitrary channel designated units. In this regard, the channel identified at 800 will represent an energy of 29 kev, while that at the channel 200 designation will exhibit an energy valuation of about 7.5 kev. The figure reveals a principal count region 130 peaking at the noted 800 channel designation which is representative of the response of the crystal and preamplifier to impinging radiation from the $^{129}I$ check source. Adjacent to the peak portion 130 is a relatively constricted region 132 leading from a skirt portion 134 of the peak region 130 to a rapidly rising noise response curve 136. As is apparent, in operating systems according to the invention, a lower energy window is elected at the region 132 and at a location there-along which permits the gathering of all data possible from the desired skirt region 134. As the lower window is, in effect, moved to the right in the sense of channel numbering or energy, count data at the skirt region 134 is effectively discarded in the interest of noise avoidance. Where CdTe crystals are utilzied as in the past, the elevation of operational temperature or environment, in effect, has evoked a movement of the noise region 136 to the right in the sense of the figure, thus requiring that the lower window threshold or energy level of the system be correspondingly moved toward and into the skirt region 134.

Figure 9:
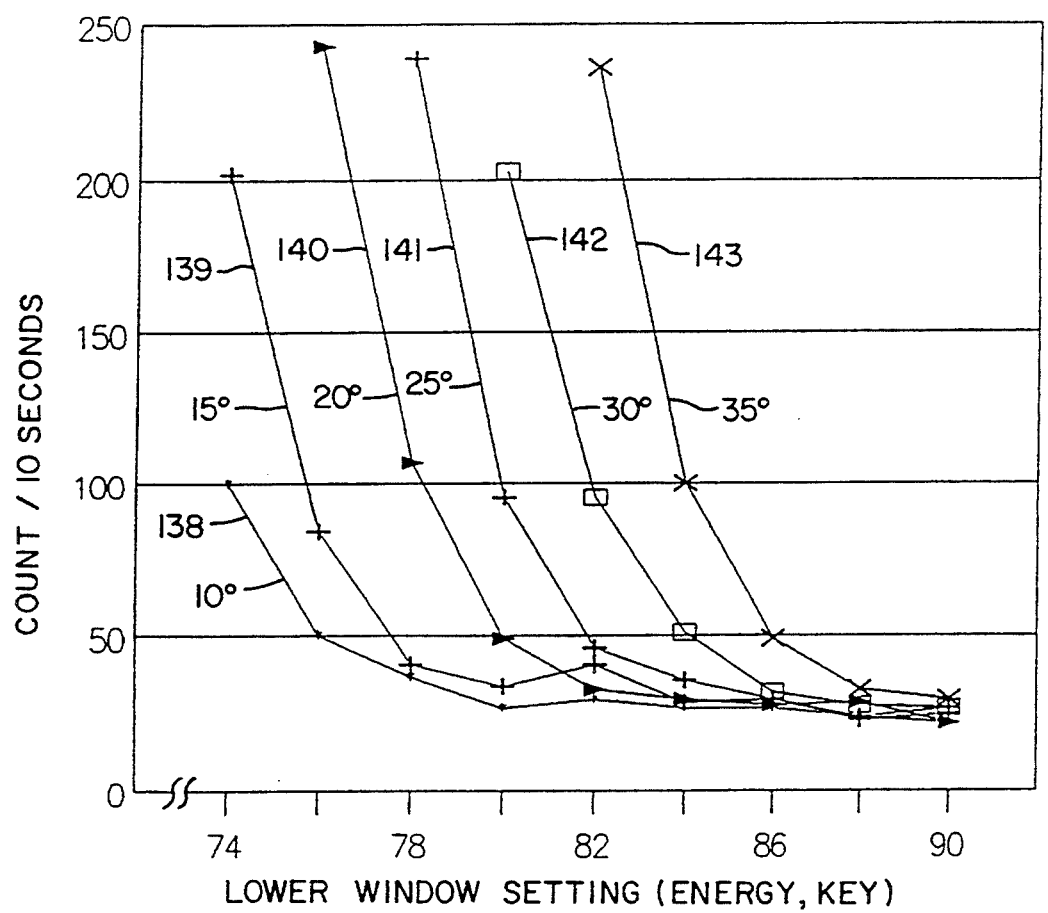
FIG. 9 is a sequence of plots of counts versus lower window settings or energy for a sequence of temperatures as applied to a CdTe crystal.

The effect of temperature upon the noise characteristic of a CdTe crystal is illustrated in connection with FIG. 9. Referring to FIG. 9, curves as at 138–143 were developed from data generated in connection with the taking of a sequence of count outputs from a CdTe crystal mounted as a probe for temperatures, respectively, of 10°, 15°, 20°, 25°, 30°, and 35° C. The horizontal scale of the chart is graduated in lower window settings for a console as described in the above-noted U.S. Pat. No. 4,801,803. The preamplification stage utilized in compiling the data also is described in that reference. In general, it has been determined that the dominant noise evolved in systems employing CdTe crystals is a characteristic of the crystal itself as opposed to being a characteristic of, for example, supporting circuitry such as a preamplification stage. In contradistinction, for the alloyed CdZnTe crystals, the opposite condition obtains, the crystals exhibiting a stability over a broader temperature ranges to the extent that noise which may generated is dominantly generated from the supporting circuitry. FIG. 9 shows that at relatively cooler temperatures, i.e. 10° C. as represented at curve 138, a broad selection of lower window settings as thresholds is available, noise development being relatively low. Thus, should the probe be used only at that temperature, the lower window or energy threshold setting can be elected at a leftward region of the chart well away from the data containing skirt component as at 134 described in conjunction with FIG. 8. Note that a noise count generally will be about 25 counts per 10 seconds as represented in FIG. 9 in conjunction with curve 138. For the surgical applications required, however, this lower temperature is not realistic. Background noise will vary radically as temperature increases. For example, increasing the temperature by 5° C. as represented at curve 139, results in an elevation of noise induced counts from about 100 to 200. Correspondingly, elevation in operation temperature to 20° C. as represented at curve 140 evokes an off-scale noise in the 400 to 500 counts per 10 second range. Accordingly, the lower window setting or lower threshold of evaluation must be moved towards the skirt component 134 as described in conjunction with FIG. 8. At room temperature, for example 25° C., the system will look for a stable lower window setting, for example, as at position 84. However, for the probe to operate at 30° C. or 35° C., then the lower window setting must be moved substantially to the right representing a much higher lower threshold of energy and a level encroaching upon the valid count data otherwise available from the skirt 134.

The preferred $Cd_{1-x}Zn_xTe$ detector crystals for the probe 16 as well as other probes exhibit very high stability with respect to noise generation when subjected to variations in temperature. Thus, these crystals are ideally suited for surgical procedures where calibration will occur at operating theater temperatures, i.e. about 15° C. and the probe devices will absorb the heat of the surgeon's hand as well as the heat emanating from the body cavity of the patient undergoing surgery, a temperature excursion amounting, for example, to about 15° or 20° C. The proportioning of the Cd component and Zn component of the improved crystals may vary to provide an effective ratio selected to suit the particular requirements of the user. However, a lower limit or boundary for the proportion of zinc wherein x equals about 0.2 has been determined, while a correspondingly high boundary or limit wherein x equals 0.8 has been determined. The alloyed crystals are marketed by Aurora Technologies Corporation, San Diego, Calif., 92067. Additional information concerning the alloyed crystals is provided in the following publications:

Butler, Lingren and Doty, "$Cd_{1-x}Zn_xTe$ Gamma Ray Detectors", IEEE Transactions on Nuclear Science, Santa Fe, N. Mex., 1991

Butler, Doty, and Lingren, "Recent Developments in CdZnTe Gamma Ray Detector Technology", Proceedings of the International Symposium of the SPIE, San Fe, N. Mex., July, 1992

Doty, Butler, Schetzina and Bowers, "Properties of Cadmium Zinc Telluride Grown by a High Pressure Bridgman Method", J. Vac. Sci. Technol., Vol. B10, June/July, 1992.

Figure 10:
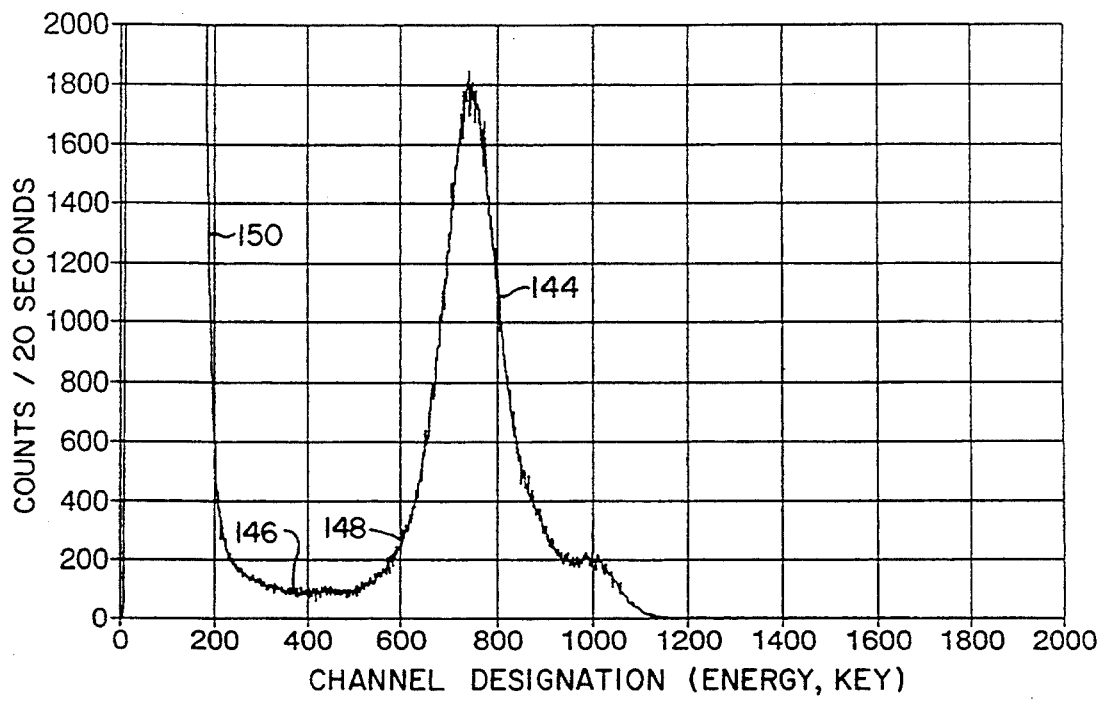
FIG. 10 is a plot developed with a multi-channel analyzer utilizing an alloyed CdZnTe crystal at 0° C.

Referring to FIG. 10, an evaluation of a $Cd_{.8}Zn_{.2}Te$ crystal employing a $^{129}I$ check source and the preamplifier described later herein is charted as the output of a multi-channel analyzer. Vertical scale in the figure represents counts per 20 second interval, while the horizontal scale, as before, represents multi-channel analyzer channel designations which, in effect, represent energy. In this regard, the radiation-based count data is derived at about 29 key and is represented as the peak region 144. Correspondingly, the relatively flat region 146 shown on the curve extending to the skirt region 148 is desirably of relatively large extent and considered to represent predominantly preamplifier noise, the latter noise being principally present at the spike region 150. The data represented by the chart at FIG. 10 was taken within an ice bath, i.e. with the alloyed crystal at 0° C.

Figure 11:
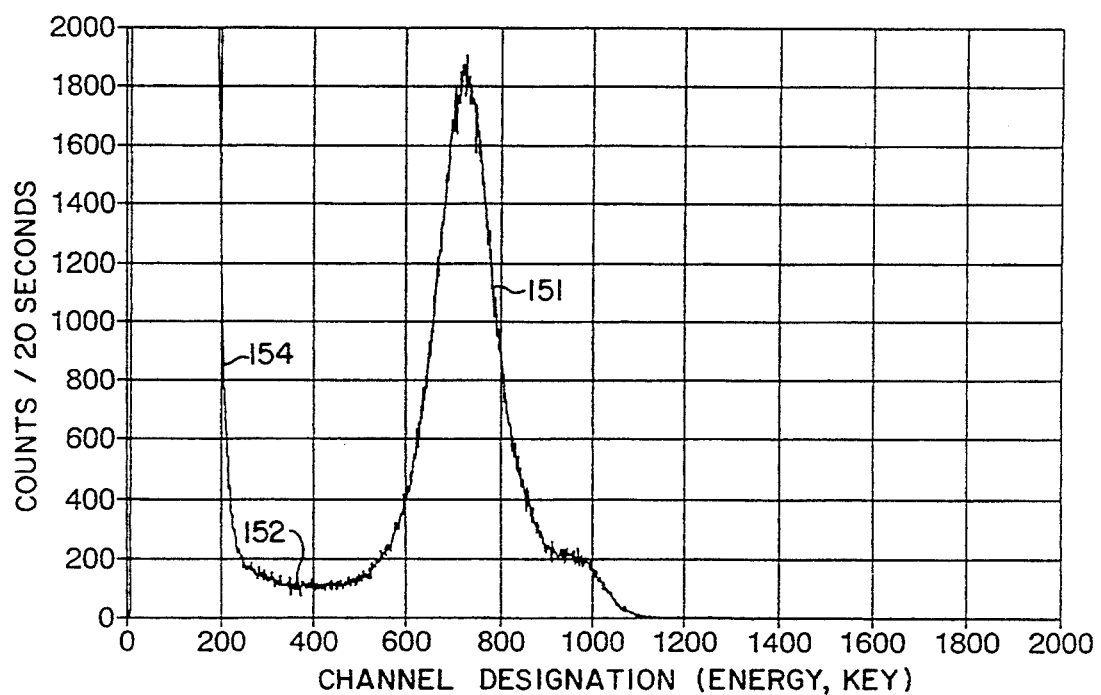
FIG. 11 is a plot corresponding to FIG. 12 but employing a CdZnTe crystal at room temperature.

Utilizing the same test set-up and the same alloyed crystal, the same crystal evaluation then was undertaken at room temperature, i.e. at 22° C. and the results plotted at FIG. 11. Note in FIG. 11 that the data collection peak region 151 remains essentially the same as that observed at 144 in FIG. 10. Similarly, the fiat region representing consistent noise at 152 remains substantially the same as that described at 146 in FIG. 10 and that the noise spike excursion 154 remains essentially the same as that shown at 150 in FIG. 10. In effect, the alloyed crystal is seen to perform with a stability over a substantial alteration of temperature. The fiat, consistent noise regions as at 152 and 146 in FIGS. 11 and 10 also represent an improvement in preamplifier performance, for example, over the performance represented at FIG. 8.

Figure 12A:
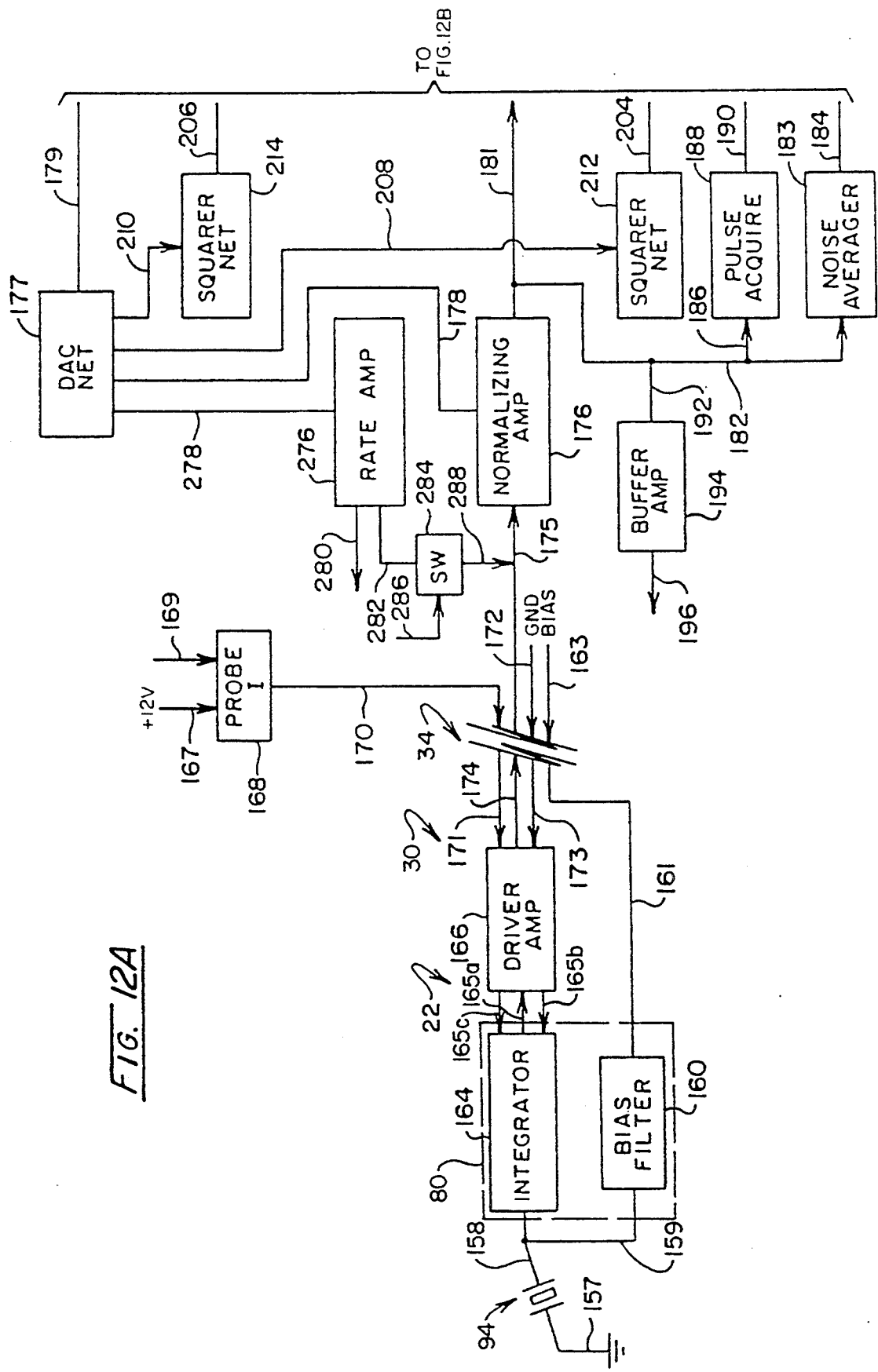
FIGS. 12A and 12B combine as labeled to form a block diagram of the functional components of a control system associated with the instrument of the invention.
Figure 12B:
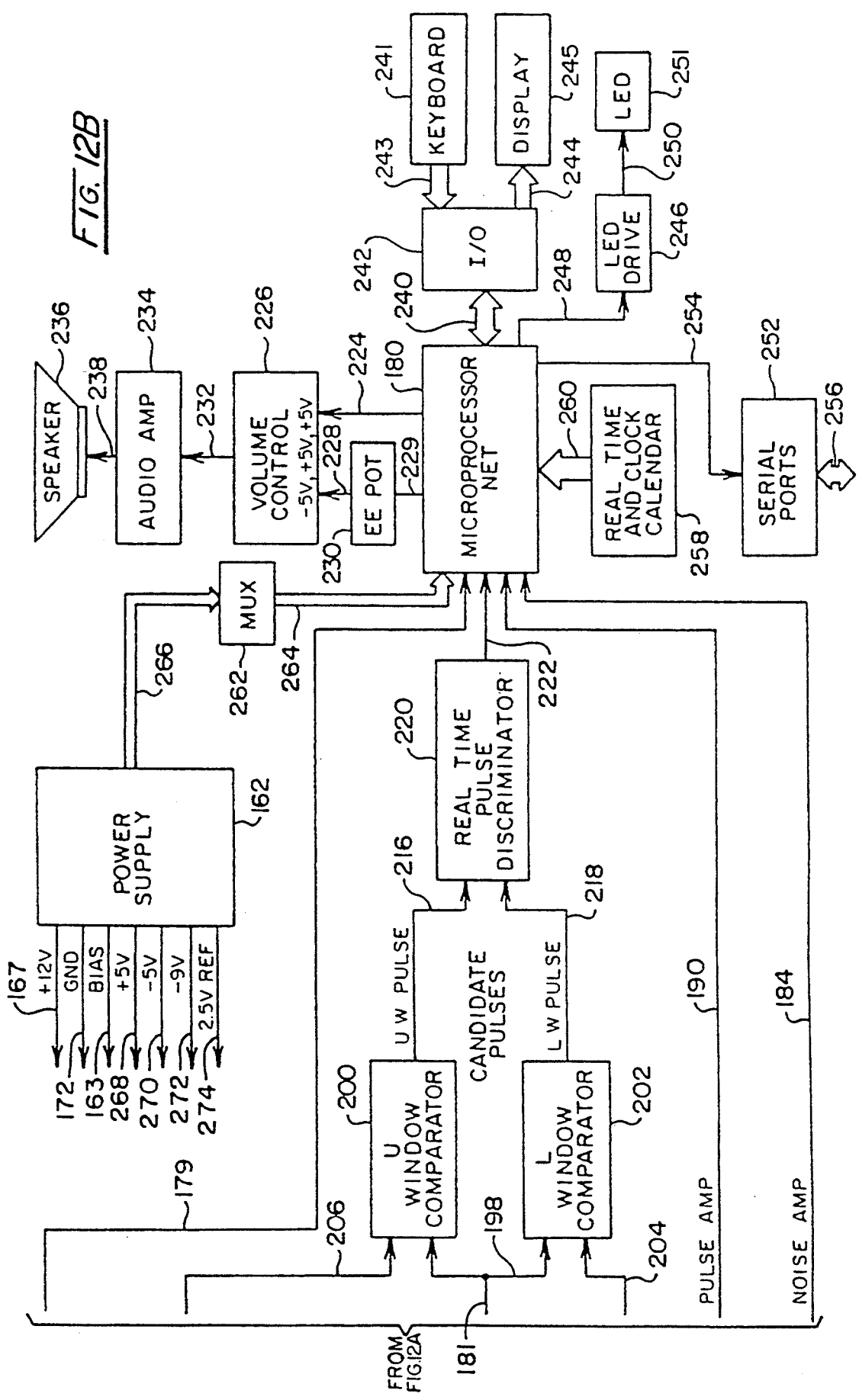

Referring to FIGS. 12A and 12B, a block diagrammatic representation of the signal treatment and control circuitry employed with the probe assembly 10 is revealed. In FIG. 12A, that crystal which is being employed, for example crystal 94, is again so labeled for this figure, and is shown having one face coupled to ground through line 157, while the opposite, biased face thereof is coupled via lines 158 and 159 to a bias filter represented at block 160. Bias filter 160 is part of the earlier-described first or initial preamplification stage 80 herein identified in FIG. 12A by a dashed boundary with the same numeration. The input to the filter 160 is derived ultimately from cable 34 (FIG. 1) and is represented in FIG. 11A at line 161 as being applied through that cable which again is represented by the numeral 34. Line 158 corresponds with the multi-strand line 106 described in connection with FIG. 7 and functions to supply an appropriate bias, for example, 80 v to the rearward surface of crystal 94. This bias emanates from a power supply shown at block 162 in FIG. 11B and represented at the labeled line 163.

Line 158 from crystal 94 is shown extending to an integrator stage 164 of the first amplifier stage 80. The integrated valuation of a detected radiation disturbance or charge characterized signal then is shown directed as represented by line 165a to a driver-amplification network shown at block 166. Line 165 additionally is part of the cable or wiring 22 as it extends along the arm 24 of surgeon 12 as discussed in conjunction with FIG. 1. Line 165a extends to a second preamplification stage described as located within a housing 30 attached, in turn, to the shoulder region 28 of the arm of the surgeon 12. Cable 22 also may carry ground and +12 v supply as shown, respectively, at lines 165b and 165c. The noted 12 v power supply as represented at line 165c is derived for the driver amplifier stage 166 from the power supply 162 (FIG. 12B) as represented at line 167 which, as shown in FIG. 12A, is directed to a probe current network represented at block 168. Under microcomputer control as represented by line 169, the network 168 develops signals, for example, determining whether the cable 34 (FIG. 1) has been properly connected to a console-based control system as described in above-noted U.S. Pat. No. 4,801,803 which is incorporated herein by reference. Delivery of the 12 v power supply for the dual stage preamplifier system is represented at line 170 as extending to the driver-amplifier stage 166 via cable 34 and line 171.

Ground to the instrument 167 also is developed from the power supply at block 162 as represented at line 172 in FIG. 12A and which is seen extending to cable 34 and via line 173 to the driver-amplification stage 166.

The output of the driver amplification stage 166 is represented at line 174 extending through the cable 34 and then is represented as line 175 to the input of a normalizing amplifier depicted at block 176. The network represented by block 176 functions to amplify or attenuate, i.e. scale the noise characteristic of any given instrument as at 16 and normalize the value thereof or render it consistent for later comparison stages. Generally, for example, the 27 kev energy level gamma ray generated pulses in a system employing $^{125}$I will be about five times higher than noise levels. Normalizing amplifier network 176 will establish those noise levels at some predetermined level, for example 200 millivolts, and the resultant proportional valid gamma related pulses will become about 1 v high for purposes of ensuing comparison functions. It may be observed that the amplifier network at block 176 is controlled from a digital-to-analog converter network represented at block 177 via line 178. Network 177, in turn, is controlled from line 179 extending, as shown in FIG. 12B, to block 180 representing a microcomputer network. The normalized output developed from network 176 is presented along lines 181 and 182 to a noise average circuit as represented at block 183. This network 183 determines an averager amplitude value for the noise of a given system with a given instrument 16 and provides a corresponding signal as represented at line 184 (noise amp) which is employed as above described as information used by the microcomputer 180. This information, in addition to being employed with the normalizing amplifier network represented at block 176, may be used to develop a low window valuation for the comparison function.

Line 182 also extends via line 186 to a pulse acquire network represented at block 188. This network functions, when activated, by the microcomputer represented at block 180, to acquire the value of the highest pulse amplitude witnessed at line 186. Periodically, this information then is transmitted to the microcomputer at block 180 as represented by line 190. Representing a form of peak detector, the network is sometimes referred to as a "snapshot circuit". Also produced from line 182, as at line 192 and block 194, is a buffer amplifier which will provide at line 196 an output representing received pulses which may be made available to the system, for example, at a console (not shown).

Line 181 extends, as shown in FIG. 12B, at line 198, to one input of an upper window comparator represented at block 200 and a lower window comparator illustrated at block 202. The threshold level for comparative purposes employed by the network at block 202 is shown asserted from line 204 and, preferably, is developed by the logic of microcomputer network 180 at a level selected above the noise amplitude signals generated from line 184. Of course, manual setting of such windows can be carried out and such setting in either event is in reliance upon the discourse presented hereinabove, for example, in connection with FIGS. 8 through 11. The upper window of acceptance for valid radiation interaction is established from a corresponding line 206. This threshold setting may be made from the information taken from pulse acquire network 188.

Returning to FIG. 12A, the upper window and lower window threshold selections are made under the control of the microcomputer network at block 180 which controls the digital-to-analog network shown at block 177. It is the characteristic of such networks as at block 177 to provide an output which is comprised, for example, of 256 steps of varying amplitude. The percentage of incrementation from step to step will vary somewhat over a range of voltage values provided. Accordingly, the outputs from this conversion network at block 177, as shown at lines 208 and 210 are directed to squarer network shown, respectively, at blocks 212 and 214. These networks function to square the current outputs at lines 208 and 210 and thus achieve a uniform percentage incrementation of the threshold defining outputs at lines 204 and 206.

Returning to FIG. 12B, the outputs of the comparator networks shown at blocks 200 and 202 represent candidate pulses which may be above or below the given thresholds and are identified as being presented as "UW PULSE" and "LW PULSE" along respective lines 216 and 218. These lines are shown directed to a real time pulse discriminator network represented at block 220 which carries out Boolean logic to determine the presence or absence of valid pulses. Valid pulses are introduced to the microcomputer network 180 as represented by line 122.

The microcomputer network represented at block 180 performs under a number of operational modes to provide both audio and visual outputs to aid the surgeon in locating and differentiating tumorous tissue. In the former regard, as represented at line 224 and block 226, a volume control function may be asserted with amplitude variations controlled from a solid-state form of potentiometer represented at line 228 and block 230. Control to potentiometer 230 is represented at line 229. Further, a "siren" type of frequency variation may be asserted as represented at line 232 to an audio amplification circuit represented at block 234 for driving a speaker as represented at 236 and line 238. With the noted siren arrangement, the frequency output from speaker 236 increases as the instrument 16 is moved closer to the situs of concentrated radiation of course, conventional clicks and beeps can be provided at the option of the operator.

The microcomputer network 180, as represented by bus-defining arrow 240 and block 242 also addresses an input-output network which, as represented at bus arrow 244, functions to provide a pulse count output of varying types as well as outputs representing volume levels, pulse height, noise levels, and battery status. These outputs are provided in visual format at a visual display represented at block 245. Similarly, the input-output function represented at block 242 provides appropriate scanning of switches or the like which may be employed with the control and are represented by block 241 and bus input arrow 243. During a given counting operation, the microcomputer network at block 180 functions to control a light emitting diode drive network represented by block 246 from line 248. The drive network represented at block 246 is shown providing an input as represented by line 250, to a light emitting diode (LED) display as represented by block 251. A serial output port of conventional variety also may be provided with the system, such ports being represented at block 252 being addressed from the microcomputer represented at block 80 from line 254 and having output and input components represented by arrow 256. A real time clock-calendar component having a non-volatile memory also may be provided in conjunction with the functions of the microcomputer network 180 as represented by block 258 and bus-arrow 260. Further, the microcomputer may be employed to monitor the performance of the power supply represented at block 162. This is shown being carried out by the interaction of the microcomputer network with a multiplexer represented at block 262 and having an association represented by arrows 264 and 266. It may be observed that the power supply also provides a +5 v source for the logic level components of the circuit as represented by line 268; a −5 v source at line 270, as well as a −9 source at line 272 for purposes of display drive, and finally, a 2.5 v reference as represented at line 274 to provide reference input for the preamplification analog circuitry.

Returning to FIG. 12A, the microcomputer network as represented at block 180 also provides an input to the digital-to-analog conversion network represented at block 177 which corresponds with the instantaneous pulse rate and this information is conveyed to a pulse rate amplifier network represented at block 276 via line 278. The resultant output, as represented at line 280, may be provided, for example, at a convenient location upon a console. This circuit represented at block 276 also may be employed to generate a calibrating pulse for testing the downstream components of the system. Thus, the microcomputer represented at block 180 applies a predetermined pulse level through the digital-to-analog conversion network at block 177 for presentation to the amplifier network represented at block 276. The resultant output at line 282 is selectively switched, as represented by block 284, to define pulse width from the microcomputer input at line 286 to generate the calibrating pulse at line 288.

Figure 13A:
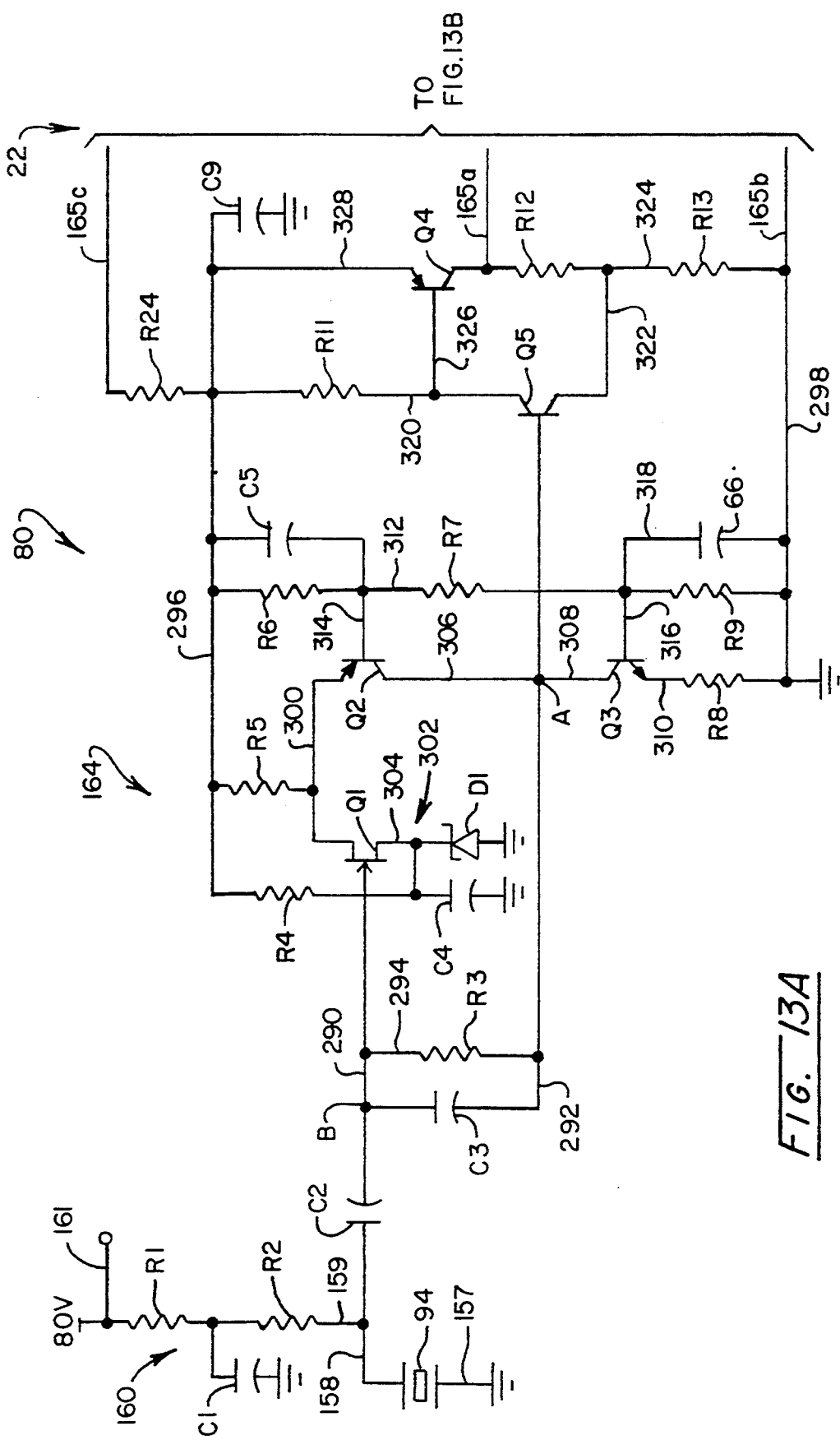
FIGS. 13A and 13B combine as labeled thereon to shown an electrical schematic diagram of a two-stage preamplifier employed with the instrument of the invention.

The diminutive, finger-ting-like structure of the probe 16 is achievable on a practical basis initially through the employment of a preamplification system which incorporates first and second stages. These stages are interconnected along the surgeon's arm by the earlier-noted cable 22 and the first stage 80 is so designed as to provide an initial signal treatment and an output topology particularly dedicated to the driving of data along the limited length of that shielded cable. The practically assembled but small size of this first stage 80 additionally is achieved through the utilization of, for example, surface mounted components. While the entire structure including the first and second stages may be formed together in a unitary fashion, for probe applications such as the present requiting a splitting of these stages, the printed circuit may be made so as to be severable at an appropriate location. The first stage is represented at FIG. 13A and the second stage is shown as such a continuation for the entire circuit in FIG. 13B. A parting line between these components of the circuit is conjunctional with the associational labeling between the two drawings.

Looking to FIG. 13A, the crystal 94 reappears with the same numeration. The upward facing surface of crystal 94 is coupled to ground as represented by line 157 which reappears from FIG. 12A. Similarly, bias is asserted to the rearward face of crystal 94 from line 158, again reappearing from FIG. 12A. An 80 v bias voltage is applied to crystal 94 through the earlier-noted bias filter 160. In this regard, the voltage is seen applied from line 161 to a decoupling network including resistor R1 and capacitor C1. This network reduces noise which might otherwise be injected from the power supply line 161. From the network incorporating capacitor C1 and resistor R1, the bias voltage is supplied through a very large value resistor R2 to lines 158 and 159. In general, the larger the resistance value of resistor R2, the smaller the amount of noise which may be contributed by that component. A small amount of current will flow through resistor R2 and its function is to maintain an appropriate bias at the crystal 94. That bias will approach the bias voltage applied from line 161. In this regard, the resistance of crystal 94 generally will be quite large. Line 158 is seen to extend to a blocking capacitor C2 functioning to block the bias voltage at the crystal 94 from the inputs of subsequent integrating or amplification stages. Accordingly, the opposite side of capacitor C2 is seen coupled via line 290 which is coupled, respectively, via lines 292 and 294 to a network including a charge accumulator capacitor C3 and a bleed resistor R3. Capacitor C3 receives the charge which is liberated by the crystal 94 in the event of a gamma strike. This voltage is witnessed, for example at node A, while the voltage at node B will have an approximately 0 value. Resistor R3 slowly bleeds the charge at capacitor C3 and, thus, has a relatively high resistance value, for example, about 200 megaohms. Such bleeding activity avoids saturation of the system. In view of the accumulation of charge with respect to capacitor C3, the first preamplifier stage generally is referred to as an integrator as described earlier in conjunction with block 164. That block numeration appears in general in conjunction with such integrating components of the instant first stage. Line 290 also is seen to extend to the gate of a junction field effect transistor (JFET) Q1. Transistor Q1, in combination with PNP transistor Q2, and NPN transistor Q3 participates in this charge accumulation at capacitor C3 of the integrator categorized stage 164. Note that +12 v from earlier-described line 165c is provided to the stage 164 from a line designated with the same numeration through resistor R24 to a line 296. Similarly, ground is asserted from along line 165b as earlier described which is indicated to extend to a line 298. In similar fashion, the output of the first preamplification stage 80 is seen, as before, at line 164a.

Line 296 extends to a connection with a resistor R5 to line 300 which is coupled between the drain terminal of transistor Q1 and the emitter of transistor Q2. Line 296 also extends through resistor R4 to a network 302 including capacitor C4 and Zener diode D1 which are coupled to the source terminal of transistor Q1 via line 304. Network 302 functions to bias the source terminal of transistor Q1 to approximately 3 v. The collector of transistor Q2 is coupled to line 306 which extends to node A at line 292. Line 306 is seen to continue as line 308 to the collector of transistor Q3 and the emitter thereof at line 310 extends through resistor R8 to ground line 298. The bases of transistors Q2 and Q3 are associated with a divider network within line 312 extending between lines 296 and 298, and incorporating resistors R6-R9. In this regard, the base of transistor Q2 is coupled via line 314 to line 312 intermediate resistors R6 and R7, while the base of transistor Q3 is coupled via line 316 to line 312 intermediate resistors R7 and R9. Thus configured, a constant voltage is applied at the base of transistor Q2 via line 314. Capacitor C5 carries out a noise reduction function at that base. In similar fashion, the junction between resistors R7 and R9 provide a bias voltage to the base of transistor Q3 via line 316. Capacitor C6 within line 318 is seen coupled from line 312 at line 316 to ground line 298 and functions to by-pass a.c. perturbations at the base of transistor Q3 to ground.

With the arrangement shown, transistors Q1 and Q2 operate as a current mirror while transistor Q3 performs as a current source. The output of the integrator function is directed via earlier-described line 292 to the base of NPN transistor Q5. Transistor Q5 in conjunction with PNP transistor Q4 constitute a non-inverting voltage amplifier with a gain of about 3. The amplifier is configured such that the collector of transistor Q5 is connected via line 320 to line 296 and incorporates a bias resistor R11. The emitter of transistor Q5 is coupled via line 322 to line 324 intermediate gain defining resistors R12 and R13. Line 324 is seen to extend between ground line 298 and the collector of transistor Q4. The latter component Q4 is configured such that its base is coupled to line 320 via line 326 and its emitter is connected to line 296 via line 328. A capacitor C9 is seen coupled to line 296. To achieve a uniformity from one preamplifier assembly to another in the instant system, the gain of this amplification stage is established by the ratio of the sum of the resistance values of resistors R12 and R13 to the resistance value of resistor R13. This arrangement avoids having a gain dependent upon the functioning of the transistor devices themselves. A desirable property of the amplifier configuration of transistors Q4 and Q5 is that the input resistance at the base of transistor Q5 is very, very large. This is provided in order to avoid the loading of the output of the circuit. Correspondingly, another advantageous property of the transistor Q5-transistor Q4 configuration resides in the aspect that the output impedance or resistance, i.e. the output resistance at the collector of transistor Q4 which is asserted at line 165a is rather low. For example, the magnitude of this output resistance is on the order of 90 ohms, a level which permits the driving of the shielded cable described in connection with FIG. 1 which extends from the probe 16 to the second preamplification stage housing 30 and is represented as being incorporated within cable line 22. In general, for the isotopes contemplated, the output voltage swing at line 165a is between 5 and 10 millivolts.

Figure 13B:
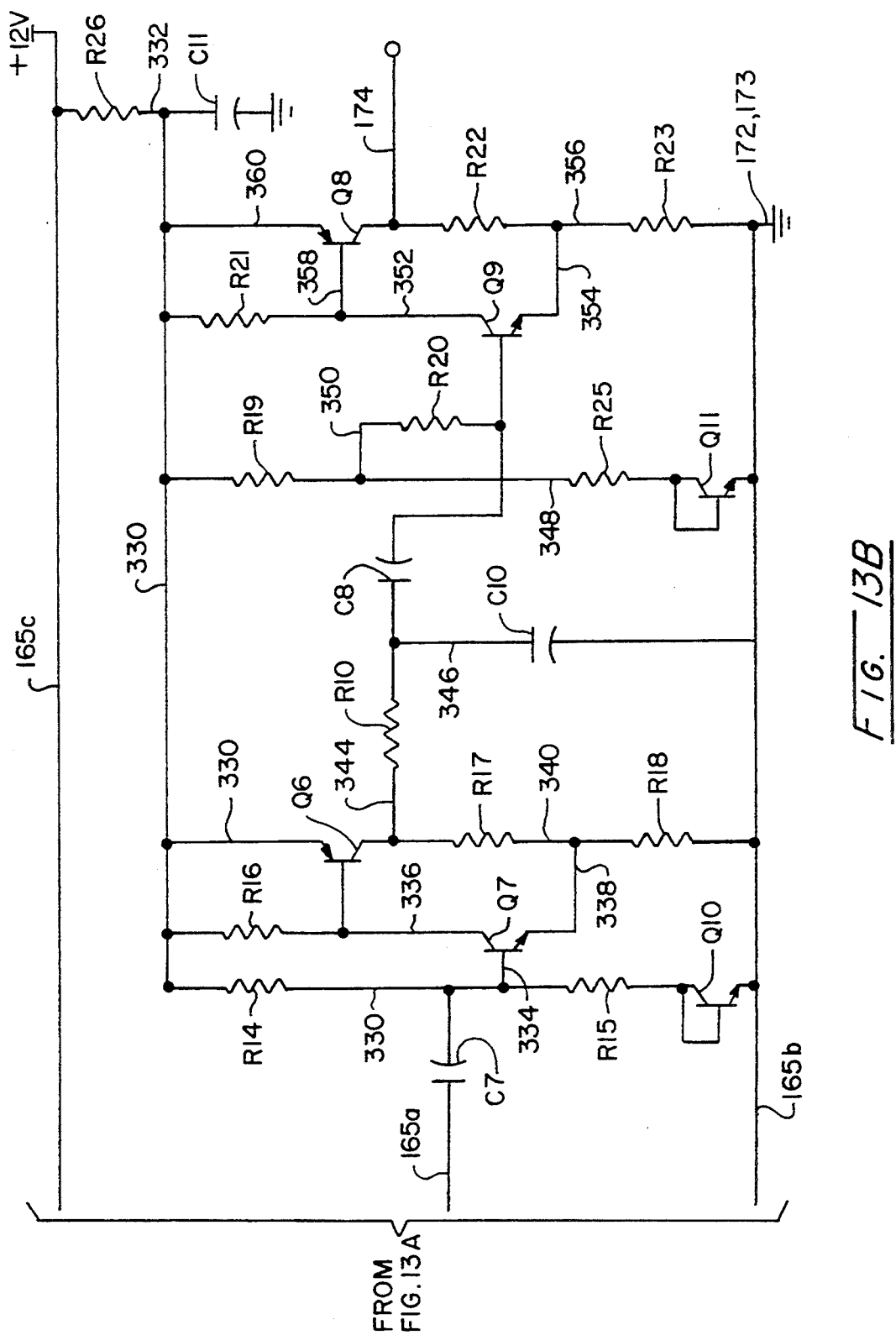

Now looking to FIG. 13B, the second preamplification stage is revealed. For the embodiment represented in FIG. 1, this stage will be incorporated within the amplification stage housing 30 affixed to the surgeon's shoulder. However, it should be understood that the entire preamplification unit represented within FIGS. 13A and 13B can be employed as a continuous circuit without the noted splitting. The task of the second preamplification stage is to provide additional gain in view of the relatively low voltages asserted at line 165a and to achieve a form of reproduction of the waveform represented by the input signal to the system and somewhat reproduced in amplified form at line 165a. Line 165a is seen directed to a network serving to carry out an approximate of differentiation which includes capacitor C7 and resistor R15 within line 330. Line 330, incorporating resistor R14, extends to line 332 and resistor R26 to +12 v supply at line 165c. A diode connected transistor Q10 is coupled within line 330 between resistor R15 and line 165b or ground. NPN device Q10 functions to retain the operating point bias at the base of NPN transistor Q7 which is seen coupled to line 330 via line 334. The peak output of the approximate differentiation evoked in conjunction with resistor R15 and capacitor C7 is considered to represent the magnitude of the charge evoked at the crystal 94 and as presented at line 334 to the base of NPN transistor Q7. Transistor Q7 and PNP transistor Q6 form an amplification stage quite similar to that described in conjunction with transistors Q4 and Q5 in FIG. 13B. To enhance a differentiation function, the input resistance at the base of transistor Q7 is rather large and the gain of the amplification stage including transistors Q6 and Q7 is controllable and selected as about 19 or 20. Note that the stage is configured such that the collector of transistor Q7 is coupled via line 336 through bias resistor R16 to line 330 while the emitter thereof is coupled via line 338 to line 340 which, in turn, is connected between the collector of transistor Q6 and ground line 165b. Line 338 is positioned intermediate resistors R17 and R18 in line 340. The emitter of transistor Q6 is coupled via line 342 to line 330 and the output of the stage at the collector thereof is present at line 344. As in the earlier case, the gain of this amplification stage is very controllable and is determined by the ratio of the resistance values of resistors R17 and R18. The output impedance at the collector of transistor Q6 is rather low, again on the order of 90 ohms. This low output impedance permits a considerable flexibility with respect to the magnitude of the components within the topology to follow. As before, the gain of the configuration of the amplification stage is quite stable, not being a function of the individual transistor devices. Output line 344 is seen to extend through resistor R10 which is associated with a capacitor C10 coupled within line 346 between line 344 and ground line 165b. Thus configured, the network including resistor R10 and capacitor C10 constitutes a low pass filter with the function of eliminating as much electrically generated noise as possible. Line 344 then is seen to extend to a coupling capacitor C8 which functions to couple the resulting voltage at the junction of resistor R10 and capacitor C10 in conjunction with resistor R20 to the input of a next amplification stage. That next amplification stage is comprised of NPN transistor Q9 and PNP transistor Q8.

Bias voltage is supplied to the base of transistor Q9 in conjunction with resistors R19, R25, and diode connected transistor Q11 in the same fashion as the bias selected with respect to transistor Q7. In this regard, note that resistors R19, R25, and transistor Q11 are coupled within line 348 between lines 330 and 165b. Resistor R20 is coupled to the base of transistor Q9 and thence via line 350 to line 348 at a location intermediate resistors R19 and R25. If there is a bias point variation at transistors Q8 and Q9, for example, as a function of temperature change, it is likely that the output of the stage would evoke a corresponding and objectionably large change. The majority of such variation resides in a change at the base-emitter voltage of transistor Q9. Transistor Q11 functions to offset that change in bias voltage to greatly reduce the temperature dependency of the amplification stage. In effect, utilization of transistors Q10 and Q11 in the circuit of FIG. 13B provides a substantial and important temperature stability for the circuit. The same form of stability is not implemented in connection with the circuit of FIG. 13A in view of the relatively low gain developed by that circuity. It may be observed additionally that with the split preamplifier approach, the longer gain stages of the amplifier are retained within a more stable temperature environment.

Now looking to the final amplification stage in detail, it may be observed that the collector of NPN transistor Q9 is coupled via line 352 through bias resistor R21 to line 330, while the emitter thereof is coupled via line 354 to line 356 which, in turn, incorporates gain defining resistors R22 and R23 and extends between line 165b and the collector of PNP transistor Q8. The base of transistor Q8 is coupled via line 358 to line 352, while the emitter thereof is coupled to line 330 via line 360. The output of the final amplification stage is provided at the collector of transistor Q8 which is seen, in turn, coupled to earlier-described line 174 (FIG. 12A) which reappears in the instant figure. In general, it is desired to set the biasing of transistors Q8 and Q9 such that the output at line 174 under queiscent conditions is just above 0 volts. This permits accommodation of energetic isotopes which may produce excursions of 8 or 10 volts.

The finger mounting probe arrangement of the invention also can be employed with different forms of radiation detectors. Looking to FIGS. 14 and 15, a sodium iodide-based finger mounted probe is represented generally at 370. Probe 370 exhibits the same appearance as the probe 16 represented in FIG. 4 and, in particular, includes a support region 372 similar to that at 52 in the earlier embodiment beneath which is located a concave mount portion 374 (FIG. 15). Elongate concave guideways 376 and 378 are located on either side of the support region 372 and generally outwardly of the concave mount portion 374. These guideways, as before, aid the surgeon in maneuvering the probe 370 about the finger when utilizing the next adjacent fingers. Just below these guideways at 376 and 378 are elongate slots, one of which is shown in FIG. 15 at 380 in FIG. 15. An identical slot is located beneath guideway 378 and these slots provide strap connector portions of the device for purposes of mounting an elastomeric web or strap 382 in the same fashion that strap 70 is connected to device 16. Just above the support portion 372 is a detector mount portion 384 within which a crystal retaining cavity 386 is formed. FIG. 14 reveals a bore through which a fiber optic bundle 390 extends in communication with the cavity 386. The base components of device 370 including the support region 372, concave mount portion 374, and the guideways 376 and 378 may be formed integrally of an opaque plastic. Over that portion, them is positioned a plastic cover 392 having a skirt portion 394 (FIG. 15) which nests against a ridge 396 (FIG. 14) formed within the support region 372. The cover may, for example, be adhesively attached to the unit 370. A sodium iodide crystal is shown in FIG. 15 at 398 being positioned within a thin lead cup 400 and retained in position within that cup 400 by a silicon rubber adhesive represented at 402. Preferably, the crystal 398 is silvered on all sides except at its light commuting contact with bundle 390. At that location as seen at 404 in FIG. 15, an optical grease may be employed to improve the transmission of light from the crystal 398 to the bunde 390. Note that a gap 406 is derived between the forward surface 408 of crystal 398 and a portion 410 of the underside of cover 392 for crystal protection. Bundle 390 extends to a photomultiplier device (not shown) which is retained within a shoulder mounted housing such as that shown at 30 in FIG. 1. The output signals from the photomultiplier device extend via cable as at 34 to a central console which may be configured as described in conjunction with FIGS. 12A and 12B. Exemplary of photomultiplier devices which may be employed with the instant probe embodiment is a Model R-1635-02 photomultiplier tube marketed by Hamamatsu Corp., Bridgewater, N.J. In general, that device has overall dimensions of about 1 cm×5 cm. Advantage further accrues with the remote location of the photo-multiplier. In this regard, such devices perform at relatively high voltage, i.e. 1000 v. By so remotely locating them, they are desirably positioned away from the patient.

Since certain changes may be made in the above-described system, apparatus, and method without departing from the scope of the invention herein involved, it is intended that all matter contained in the description thereof or shown in the accompanying drawings shall be interpreted as illustrative and not in a limiting sense.

We claim:

1. A surgical probe instrument for locating and differentiating tissue at which a locator is concentrated, comprising:

a finger mount having a support region and an oppositely disposed finger mount portion configured for slideable positioning and retention upon a portion of a finger of a surgeon, and a detector mount portion positioned at said support region having a crystal retainer comprised of materials attenuating radiation at predetermined energy levels less than about 150 Kev, said detector mount portion having a detector seat and sidewalls extending to a forward opening;

a crystal detector mounted at said detector seat for response to radiation impinging thereon only from said forward opening to provide a detector output;

a window transmissive of said radiation, mounted over said detector mount portion;

transmission means responsive to said detector output for providing a transmit pulsed output; and a control system coupled with said transmission means in a manner receiving said pulsed output for validating said transmit pulsed output with respect to said predetermined energy levels to identify valid pulses, said system computing the rate of said valid pulses and generating an audible output audibly perceptible to the surgeon at a frequency selected to correspond with said rate.

2. The probe instrument of claim 1 in which finger mount portion includes at least one externally disposed guideway configured for stabilizing abutting engagement with a said finger of the surgeon.

3. The probe instrument of claim 1 in which said finger mount portion is concave and configured substantially as a half-cylindrical surface of curvature selected for nesting against said surgeon's finger.

4. The probe instrument apparatus of claim 3 in which:

said finger mount portion extends to two, spaced apart and oppositely disposed strap connector portions; and including a flexible retainer strap connected across said half-cylindrical surface to said strap connector portions and configured for retaining said finger mount portion in slideable engagement against said select finger.

5. The probe instrument of claim 1 in which said finger mount portion includes elastomeric retainer means for alternately retaining said finger mount in an operative orientation adjacent an outward portion of the select finger wherein said window is positioned upwardly of the underside of the select finger, and said finger mount being slidably movable to a standby orientation adjacent the inward portion of the select finger wherein said window is positioned outwardly of the upper side of the select finger.

6. The probe instrument of claim 1 in which:
said finger mount support region includes a circuit enclosure;
said transmission means includes a first pre-amplification stage mounted within said circuit enclosure, having an input coupled with said crystal detector and responsive to said detector output to provide a first amplified output, a circuit housing located remotely from said finger mount, a second preamplification stage within said circuit housing generating said transmit pulsed output, and a first cable coupled in electrical communication between said first pre-amplification stage and said second pre-amplification stage.

7. The probe instrument of claim 6 in which:
said circuit housing includes a connector for effecting its mounting at the arm of the surgeon remotely from the fingers; and
said first cable is of a restricted length selected for extending between said first and second pre-amplification stages.

8. The probe instrument of claim 7 including a second cable of length greater than said first cable, coupled between said second preamplifier stage and said control system for conveying said transmit pulsed output thereto. standby orientation adjacent the inward portion of the select finger wherein said window is positioned outwardly of the upper side of the select finger.

9. The probe instrument of claim 6 in which said first preamplification stage comprises:
a charge accumulating network coupled with said crystal detector and providing a charge responsive voltage signal in response to said detector output; and
a first voltage amplifier stage electrically coupled with said charge accumulating network for response to said charge responsive voltage signal for producing a first amplifier voltage signal, said first voltage amplifier stage providing an output conveyed by said first cable, said output exhibiting a low output impedance selected for transmitting said first amplified voltage signal through said first cable.

10. The probe instrument of claim 9 in which said second preamplification stage comprises:
a second voltage amplifier stage, having a first bias point value dependent gain selected to provide a second amplified voltage signal, and first temperature responsive solid-state means for stabilizing said first bias point value under conditions of environmental temperature change; and
a third voltage amplifier stage coupled with to said second voltage amplifier stage, having a second bias point value dependent gain selected for a predetermined amplification of said second amplified voltage signal, and second temperature responsive solid-state means for stabilizing said second bias point value under conditions of environmental temperature change.

11. The probe instrument of claim 1 in which said crystal detector is a cadmium-zinc-telluride crystal.

12. The apparatus of claim 1 in which:
said crystal detector is a sodium chloride crystal deriving said detector output as scintillations;
said transmission means comprises a fiber optic transmission cable having one end coupled in light transmitting relationship with said crystal detector and extending a predetermined distance to an output end, a housing located removably from said finger mount, a photo-multiplier mounted within said housing having an input coupled in light receiving relationship with said fiber optic transmission cable opposite end and having an output deriving said transmit output.

13. The apparatus of claim 12 in which:
said housing includes a connector for effecting its mounting at the arm of the surgeon remotely from the fingers; and
said fiber optic transmission cable is of a restricted length selected for extending between said detector crystal and said housing.

14. The apparatus of claim 13 including a communication cable of length greater than said transmission cable coupled between said photo-multiplier output and said control means for conveying said transmit output thereto.

15. An instrument for detecting and locating sources of radiation emission at predetermined energy levels while within a surgical environment, comprising:
a housing having a forward support region;
a crystal retainer assembly supported by said forward support region;
a cadmium-zinc-telluride crystal having forwardly and rearwardly disposed faces, mounted by said crystal retainer assembly and having said Zn component alloyed with Cd and Te components in an amount effective to permit a substantial threshold-based avoidance of electrical noise, and generating a detector output in response to radiation emission;
transmission means for applying electrical ground to said crystal forward face and an electrical bias to said crystal rearward face and including a preamplifier for conveying and treating said detector output to provide a transmitted output, said preamplifier comprising:
a charge accumulating network coupled with said crystal and providing a charge-responsive voltage signal in response to said detector output,
a first voltage amplifier electrically coupled with said charge accumulating network for response to said charge responsive voltage signal to generate a first amplified voltage signal at an output;
a second voltage amplifier stage electrically coupled with said first voltage amplifier stage output for response to said first amplified voltage signal, providing a first bias point value dependent gain selected to produce a second amplified voltage signal, and first temperature responsive solid-state means for effecting a stabilization of said first bias point value under conditions of environmental temperature change;

a third voltage amplifier stage electrically coupled with said second voltage amplifier stage for response to said second amplified voltage signal, providing a second bias point value dependent gain selected to effect a predetermined amplification of said second amplified voltage signal, and second temperature responsive solid-state means for effecting a stabilization of said second bias point value under conditions of environmental temperature change; and control means responsive to said transmitted output for providing a perceptible output corresponding therewith.

16. The instrument of claim 15 in which:

said charge accumulating network and said first voltage amplifier stage are mounted with said housing;

including a remote circuit housing located remotely from said housing, within which said second and third voltage amplifier stages are mounted;

a first cable of selectively restricted length coupled in electrical communication between said first voltage amplifier stage output and said second voltage amplifier stage;

said first amplifier stage output exhibiting a low output impedance selected for transmitting said first amplifier voltage signal through said first cable; and including a second cable of length greater than said restricted length of said first cable electrically coupled with said third voltage amplifier stage and extending from said remote circuit housing to and in electrical communication with said control means for conveying said transmitted output thereto.

17. Apparatus for determining the site of a locator within a patient, comprising:

a housing having a forward support region;

a crystal retainer assembly supported by said forward support region;

a cadmium telluride crystal having forwardly and rearwardly disposed faces mounted by said crystal retainer assembly and generating a detector output in response to radiation emitting at predetermined energy levels from said locator;

a grounding contact electrically coupled with said forwardly disposed surface;

an electrical biasing contact electrically coupled with said rearwardly disposed surface;

a pre-amplifier, including:

a charge accumulating network coupled with said electrical biasing contact and providing a charge-responsive voltage signal in response to said detector output, a first voltage amplifier stage electrically coupled with said charge accumulating network for response to said charge responsive voltage signal for producing a first amplified voltage signal at an output, a second voltage amplifier stage electrically coupled with said first voltage amplifier stage output for response to said first amplified voltage signal, providing a first bias point value dependent gain selected to derive a second amplified voltage signal, providing a first bias point value dependent gain selected to produce a second amplified voltage signal, and first temperature responsive solid-state means for effecting a stabilization of said first bias point value under conditions of environmental temperature change, and a third voltage amplifier stage electrically coupled with said second voltage amplifier stage for response to said second amplified voltage signal, providing a second bias point value dependent gain selected to effect a predetermined amplification of said second amplified voltage signal to generate a third amplified voltage signal, and a second temperature responsive solid-state means for effecting a stabilization of said second bias point value under conditions of environmental temperature change; and a control circuit coupled with said third voltage amplifier stage for treating said third amplified voltage signal to generate an emission count based perceptible output.

18. The apparatus of claim 17 in which said crystal detector is a cadmium-zinc-telluride crystal.

19. The apparatus of claim 18 in which said cadmium-zinc-telluride crystal can be represented by the formula: $Cd_{1-x}Zn_xTe$, where the value of x ranges from about 0.2 to about 0.8.

20. The apparatus of claim 19 in which said value of x is about 0.2.

21. The apparatus of claim 17 in which said housing is configured as a finger mount with a finger mount portion located oppositely from said support region, said finger mount portion being configured for slidable positioning and retention upon a portion of a human finger.

22. The apparatus of claim 21 in which said finger mount portion includes elastomeric retainer means for alternately retaining said finger mount in an operative orientation adjacent an outward portion of the finger wherein said crystal forwardly disposed face is oriented outwardly of the underside of the finger, and said finger mount being slidably movable to a standby orientation adjacent the inward portion of the finger wherein said crystal forwardly disposed face is positioned outwardly of the upper side of the finger.

* * * * *